US012599491B2

(12) United States Patent
Bluecher et al.

(10) Patent No.: US 12,599,491 B2
(45) Date of Patent: **\*Apr. 14, 2026**

(54) BILIARY STENT

(71) Applicant: BVW Holding AG, Cham (CH)

(72) Inventors: Lukas Bluecher, Eurasberg (DE);
Michael Milbocker, Holliston, MA
(US)

(73) Assignee: BVW Holding AG, Cham (CH)

( * ) Notice: Subject to any disclaimer, the term of this
patent is extended or adjusted under 35
U.S.C. 154(b) by 958 days.

This patent is subject to a terminal dis-
claimer.

(21) Appl. No.: 17/838,407

(22) Filed: Jun. 13, 2022

(65) Prior Publication Data

US 2022/0409408 A1 Dec. 29, 2022

Related U.S. Application Data

(63) Continuation of application No. 16/524,344, filed on
Jul. 29, 2019, now Pat. No. 11,382,776.
(Continued)

(51) Int. Cl.
A61F 2/848 (2013.01)
A61F 2/00 (2006.01)
(Continued)

(52) U.S. Cl.
CPC .............. A61F 2/90 (2013.01); A61F 2/0077
(2013.01); A61F 2/848 (2013.01); A61L 31/14
(2013.01);
(Continued)

(58) Field of Classification Search
CPC ............ A61F 2/0077; A61F 2002/0081; A61F
2002/0086; A61F 2002/041; A61F 2/848;
(Continued)

(56) References Cited

U.S. PATENT DOCUMENTS

| 5,118,394 A | 6/1992 | Makino et al. |
| 5,776,160 A | 7/1998 | Pasricha et al. |

(Continued)

FOREIGN PATENT DOCUMENTS

| TW | 201323026 A | 6/2013 |
| WO | 2010096073 A1 | 8/2010 |
| WO | 2018126238 A1 | 7/2018 |

OTHER PUBLICATIONS

Search Report & Written Opinion of corresponding International
application No. PCT/US2019/043869, dated Oct. 9, 2019, 14 pages.

*Primary Examiner* — Leslie A Lopez
(74) *Attorney, Agent, or Firm* — Patterson Intellectual
Property Law, P.C.; Ryan D. Levy; Mark A. Kilgore

(57) ABSTRACT

The present disclosure provides an endoprosthesis where a
preferably polymeric coating has a number of surface fea-
tures such as protrusions or textures that are arranged in a
micropattern. The endoprosthesis optionally has an
expanded state and a contracted state, and in some cases
includes a stent with a polymeric coating attached to an outer
surface of the stent. The stent may have an inner surface
defining a lumen, an outer surface, and a stent thickness
defined between the inner surface and outer surface. The
stent may comprise a plurality of surface textures extending
from the stent surfaces, wherein the textures are arranged in
a macropattern.

20 Claims, 8 Drawing Sheets

Related U.S. Application Data

(60) Provisional application No. 62/711,539, filed on Jul. 29, 2018.

(51) Int. Cl.

| | |
|---|---|
| *A61F 2/04* | (2013.01) |
| *A61F 2/90* | (2013.01) |
| *A61L 31/14* | (2006.01) |
| *A61L 31/08* | (2006.01) |

(52) U.S. Cl.
CPC . *A61F 2002/041* (2013.01); *A61F 2220/0008* (2013.01); *A61F 2250/0056* (2013.01); *A61L 31/08* (2013.01)

(58) Field of Classification Search
CPC ..... A61F 2220/0008; A61F 2250/0056; A61L 2400/18
See application file for complete search history.

(56) References Cited

U.S. PATENT DOCUMENTS

| | | | |
|---|---|---|---|
| 5,876,450 A | 3/1999 | Johlin, Jr. | |
| 5,968,070 A | 10/1999 | Bley et al. | |
| 6,383,217 B1 | 5/2002 | Satz | |
| 6,547,814 B2 | 4/2003 | Edwin et al. | |
| 6,746,489 B2 | 6/2004 | Dua et al. | |
| 7,041,127 B2 | 5/2006 | Ledergerber | |
| 7,182,745 B2 | 2/2007 | Desmond, III | |
| 7,273,493 B2 | 9/2007 | Ledergerber | |
| 7,316,709 B2 | 1/2008 | Limon | |
| 7,875,068 B2 | 1/2011 | Mangiardi et al. | |
| 7,914,568 B2 | 3/2011 | Cully et al. | |
| 7,967,770 B2 | 6/2011 | Li et al. | |
| 7,972,261 B2 | 7/2011 | Lamoureux et al. | |
| 8,206,433 B2 | 6/2012 | Rucker | |
| 8,955,520 B2 | 2/2015 | Devereux et al. | |
| 8,968,765 B2 | 3/2015 | Chen et al. | |
| 9,120,670 B2 | 9/2015 | Hulseman et al. | |
| 9,226,812 B2 | 1/2016 | Anai et al. | |
| 9,492,573 B2 | 11/2016 | Gonzales | |
| 9,908,274 B2 | 3/2018 | Hulseman et al. | |
| 9,987,398 B2 | 6/2018 | Garza | |
| 9,988,201 B2 | 6/2018 | Darin et al. | |
| 10,377,044 B2 | 8/2019 | Hulseman et al. | |
| 10,458,053 B2 | 10/2019 | Hulseman et al. | |
| 10,575,667 B2 | 3/2020 | Hulseman et al. | |
| 10,687,642 B2 | 6/2020 | Hulseman et al. | |
| 10,889,005 B2 | 1/2021 | Hulseman et al. | |
| 2003/0036794 A1 | 2/2003 | Ragheb et al. | |
| 2005/0154448 A1 | 7/2005 | Cully et al. | |
| 2007/0038292 A1 | 2/2007 | Danielpour | |
| 2008/0051911 A1 | 2/2008 | Rucker | |
| 2008/0208312 A1 | 8/2008 | Kwitkin et al. | |
| 2008/0319540 A1 | 12/2008 | Jordan et al. | |
| 2009/0099646 A1 | 4/2009 | Matsuda et al. | |
| 2009/0187240 A1 | 7/2009 | Clerc et al. | |
| 2009/0312834 A1 | 12/2009 | Wood et al. | |
| 2010/0049291 A1 | 2/2010 | Yampolsky et al. | |
| 2010/0137673 A1 | 6/2010 | Srivastava et al. | |
| 2010/0137970 A1 | 6/2010 | Srivastava et al. | |
| 2012/0150277 A1 | 6/2012 | Wood et al. | |
| 2012/0226344 A1 | 9/2012 | Shirokaze et al. | |
| 2013/0190706 A1 | 7/2013 | Kleiner | |
| 2013/0245747 A1 | 9/2013 | Jordan et al. | |
| 2014/0088622 A1 | 3/2014 | Rousseau | |
| 2014/0277395 A1* | 9/2014 | Firstenberg | A61F 2/06 623/1.36 |
| 2014/0343683 A1 | 11/2014 | Jeon et al. | |
| 2014/0379092 A1 | 12/2014 | Anai et al. | |
| 2015/0051693 A1 | 2/2015 | Bertolino et al. | |
| 2015/0368838 A1 | 12/2015 | Hulseman et al. | |
| 2016/0317330 A1 | 11/2016 | Clerc et al. | |
| 2017/0014111 A1* | 1/2017 | Hulseman | A61B 17/00 |
| 2017/0065398 A1 | 3/2017 | Bertolino et al. | |
| 2017/0231749 A1 | 8/2017 | Perkins et al. | |
| 2018/0147321 A1 | 5/2018 | Bluecher et al. | |
| 2019/0062155 A1 | 2/2019 | Hulseman et al. | |
| 2020/0338808 A1 | 10/2020 | Hulseman et al. | |
| 2021/0086371 A1 | 3/2021 | Hulseman et al. | |

* cited by examiner

BILIARY STENT

CROSS-REFERENCES TO RELATED APPLICATIONS

This application claims benefit of the following patent application(s) which is/are hereby incorporated by reference: U.S. patent application Ser. No. 16/254,344 filed Jul. 29, 2019, and U.S. Provisional Application No. 62/711,539 filed on Jul. 29, 2018.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

The present invention relates generally to a biliary or gastrointestinal stent.

More particularly, this invention pertains to an endoprosthesis where a polymeric coating has a number of surface features such as protrusions or textures that are arranged in a micropattern.

Stents are frequently used to enlarge, dilate or maintain the patency of narrowed body lumens. A stent may be positioned across a narrowed region while the stent is in a compressed state. The stent may then be expanded in order to widen the lumen. Stents used in the gastrointestinal system are commonly constructed of plastic or coated metal wire. Plastic and coated metal wire stents facilitate retrieval and/or replacement of the stent during a follow-up procedure.

Plastic stents are not as easily expanded like metal wire stents. That is, plastic stents generally have a fixed diameter. Since plastic stents are frequently delivered through the working channel of an endoscope, the diameter of the working channel limits the diameter of the stent. For example, plastic stents typically have a gauge that is no greater than 11.5 French. However, such a small gauge stent rapidly becomes clogged within the biliary and pancreatic ducts, thereby requiring replacement every three months, or even sooner.

In the case of the coated metal wire stent, there is less limitation on the diameter of the stent when it is deployed since metal wire stents can be compressed and then expanded at the delivery site. However, these stents, as well as the plastic stents, have issues of migration.

To secure the stent at a site of implantation within the body lumen, the tubular member may include a means for retaining the stent within a body lumen, such as retention flaps radially projecting from the tubular body. While the openings for the retention flaps and the stent generally may provide access to the interior of the stent, cellular or other material may also access the stent's interior and tend to develop into an obstruction and restricting flow through the stent.

Alternatively, stents may include one or more curled or coiled end portions. One such example is shown by U.S. Pat. No. 5,052,998 to Zimmon which discloses an indwelling drainage stent having flaps at one end, a series of drainage perforations along the length of the drainage stent, and a pigtail configuration at the opposite end. Other stents include anchoring flaps or pigtail loops at both ends of the stent. Stent geometry and physical characteristics may be dramatically affected by the need to anchor the stent within the body lumen using the flaps or curled ends, causing prior art devices to be suboptimal.

For example, during the placement procedure, conventional structures for retaining the stent within the body passage, such as flaps or curled ends, may irritate ductal tissue as they pass through the duct, which may lead to inflammation of the duct. Conventional stent structures for retaining the stent in position after implantation may also cause aggravation to the ductal tissue while the stent is left in place, or when the stent is removed. Furthermore, insertion and placement of a stent placed by endoscopic sphincterotomy may require stretching and cutting of certain areas of the gastrointestinal tract. Such operations may compromise the function of the gastrointestinal system and may also lead to duodeno biliary reflux.

Therefore, there exists a need for an improved stent device which can be adequately retained within a body vessel, such as a biliary or pancreatic duct, with increased resistance to fouling, reduced reliance on insufficient anchoring mechanisms, reduced irritation to the body tissue, and which may be inserted, maintained, and/or removed without damaging the body vessel. Furthermore, there exists a need for an improved method or procedure of implanting the drainage device enabled by a stent design which does not require compromising the gastrointestinal system and reducing the risk of duodenal biliary reflux.

BRIEF SUMMARY OF THE INVENTION

The present disclosure provides an endoprosthesis where a preferably polymeric coating has a number of surface features such as protrusions or textures that are arranged in a micropattern. As used herein, a micropattern may include a regular or irregular array of micro-scale features (e.g., protrusions such as micropillars, voids such as textures). These micropatterns are disposed hierarchically on the stent. As used herein, "hierarchical" means patterns of characteristic dimension are stack, the larger dimension pattern feature supporting smaller dimension pattern features. Generally, micro-scale feature means a feature having a dimension (e.g., length, width, or height) in a range of from about 1 micrometer to about 10,000 micrometers. Herein, unless the context indicates otherwise, micro-scale features are collectively referred to as surface texture. In one or more embodiments disclosed herein, a biointeractive micropatterned stent coating may provide a solution for maintaining luminal patency while including potential for removability and reducing migration.

The present invention relates to an article, including adhesive surfaces bearing a microstructured surface wherein the microstructured surface comprises at least two kinds of features and wherein the lateral aspect ratio of the features range from about 0.1 to about 10 for each feature, and at least one feature dimension varies by at least a factor of 10%. For example, two sets of pillars, one 5 microns in diameter and 30 microns tall and another set of pillars >15 microns in diameter and 75 microns tall, wherein the first set of pillars is disposed on the top surface of the second set of pillars. At least two of the feature dimensions (height, width and length) must be microscopic. All three of the feature dimensions (height, width, length) may be microscopic.

In at least one embodiment, an endoprosthesis, has optionally an expanded state and a contracted state, and in some cases includes a stent with a polymeric coating attached (e.g., adhered, etc.) to an outer surface of the stent. The stent has an inner surface defining a lumen. The stent has an outer surface and a stent thickness defined between the inner surface and outer surface. The stent comprises a plurality of surface textures extending from the stent surfaces, wherein the textures are arranged in a macro pattern. The micro pattern may reside on the exterior surface and/or the interior surface. Micro pattern on the exterior surface anchor the stent. Micro pattern on the interior surface resists fouling. In at least one embodiment, the stent is a flared stent.

The polymeric coating includes a base and a tissue engagement portion. The base includes a first surface (e.g., attached to the outer surface of the stent). The tissue engagement portion includes a second surface facing outwardly from the stent (e.g., in a direction opposite of the first surface). The tissue engagement portion includes a structure that defines a plurality of protrusions or wells extending outwardly/inwardly from the second surface away/toward the base. In at least one embodiment, the surface textures are arranged in a micropattern. In one or more embodiments, the base and the stent are coterminous. In one or more embodiments, the base may cover the apertures of the stent. When the endoprosthesis is expanded or in the implantation configuration in a lumen defined by a vessel wall, the structure defining the plurality of surface textures generates an adhesive force that creates an interlock between the vessel wall and the endoprosthesis.

In one or more embodiments, the stent surface may include a plurality of protrusions (e.g., micro pillars) of at least two scale dimensions extending from the base (e.g., outwardly from the stent) and arranged hierarchically. In one or more embodiments, the protrusions may be arranged in a regular micro pattern (e.g., of micro pillars).

In a preferred embodiment, the interior stent surface is a modulated hydrophobic/hydrophobic surface and the exterior surface is a modulated hydrophobic/hydrophilic surface, wherein each surface may be described as a hierarchical patterned surface designed to a specific biologic interface.

The micro pattern is specifically designed for a particular tissue in order to effectively localize the stent to the target tissue. In at least one embodiment, the micro pattern is present along at least a portion of the endoprosthesis. In at least one embodiment, the texture of the micropattern can be uniform or the micro pattern can be formed of texture having a first configuration and texture having at least a second configuration.

In at least one embodiment, the textures of the micro pattern are at least two types of cylindrical pillars, each cylindrical pillar having a diameter and a height, wherein the diameter of each cylindrical pillar is equal to 0.1 to 1 times its height. The pillars are stacked hierarchically and arranged to an offset rectangular grid pattern and disposed on a sinusoidally varying substrate.

In at least one embodiment, each texture of the micropattern has a first dimension and a second dimension, wherein the first dimension is between about 1 micron and 1000 microns (e.g., between about 1 micron and 100 microns), wherein the second dimension is between about 1 micron and 1000 microns (e.g., between about 10 microns and 150 microns), and wherein one texture is entirely disposed on top of the other texture, wherein a ratio between the pitch of the first texture and the pitch of the second texture is between about 0.1 and 0.5. In at least one embodiment, each protrusion has a ratio between the first dimension and the second dimension that is between about 0.2 and 0.3.

In one embodiment, the present invention incorporates a textured surface stent device, which may allow for sufficient anchoring while reducing the risk of migration, and additionally allows for shifting and/or removal of the stent after implantation.

An endoluminal stent graft may include one or more segments of a healing promoter attached within a proximal anchor region of an endoluminal stent graft, and, optionally, within one or more distal anchor regions. The healing promoter may be a chemical disposed in an absorbable layer, or simply a second textured surface designed to direct a specific type of cellular ingrowth. The healing promoter may be a tissue scaffold. When the endoluminal stent graft is positioned within a lumen, the segments of the healing promoter promote and guide the migration, proliferation and adhesion of vessel cells to the endoluminal stent graft to increase localized healing. Thus, healing time after implant of an endoluminal stent graft may be decreased and a more stable implant produced that is less susceptible to migration and/or endoleaks that could otherwise form at the sides of the proximal neck.

DETAILED DESCRIPTION OF THE INVENTION

Figure 1:
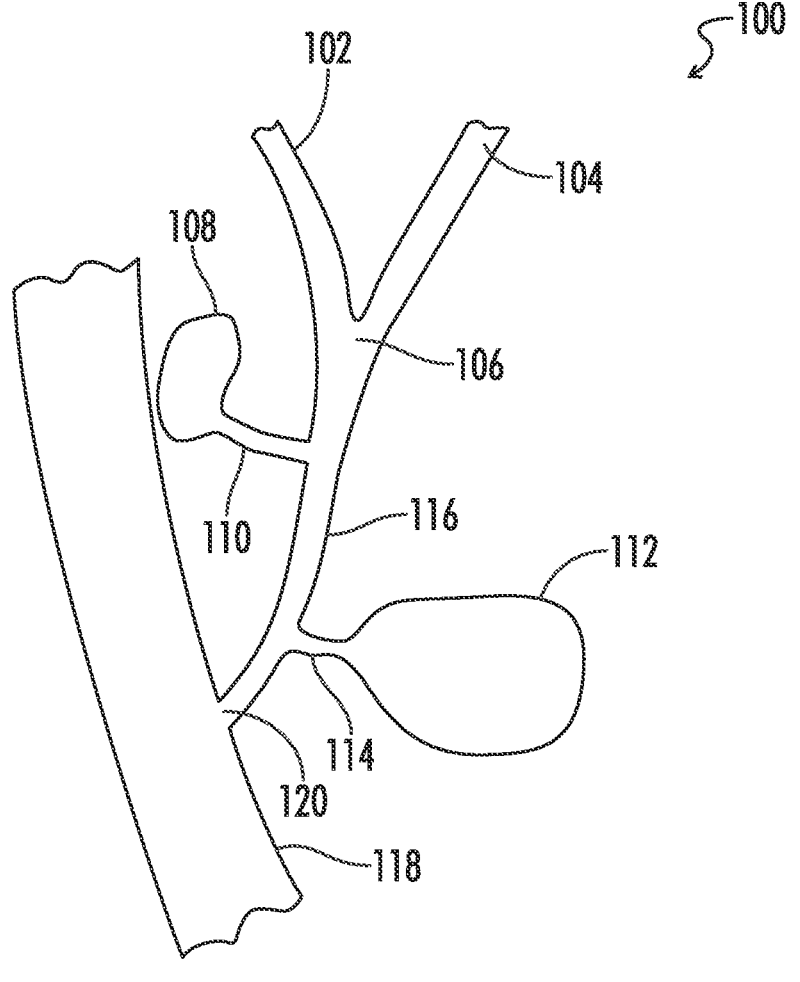
FIG. 1 is an illustration of a typical biliary system.

Reference will now be made in detail to the embodiments of the present disclosure, one or more examples of which are set forth herein below. Each embodiment and example is provided by way of explanation of the device, composition, and materials of the present disclosure and is not a limitation. Rather, the following description provides a convenient illustration for implementing exemplary embodiments of the disclosure. In fact, it will be apparent to those skilled in the art that various modifications and variations can be made to the teachings of the present disclosure without departing from the scope or spirit of the disclosure. For instance, features illustrated or described as part of one embodiment, can be used with another embodiment to yield a still further embodiment. Thus, it is intended that the present disclosure covers such modifications and variations as come within the scope of the appended claims and their equivalents. Other objects, features, and aspects of the present disclosure are disclosed in or are obvious from the following detailed description. It is to be understood by one of ordinary skill in the art that the present discussion is a description of exemplary embodiments only and is not intended as limiting the broader aspects of the present disclosure.

In the present application, the term "proximal" may refer to a direction that is generally towards a physician during a medical procedure, while the term "distal" refers to a direction that is generally towards a target site within a patient's anatomy during a medical procedure.

As used herein the terms "comprise(s)," "include(s)," "having," "has," "contain(s)," and variants thereof, may be open-ended transitional phrases, terms, or words that do not preclude the possibility of additional acts or structure.

As used herein, the term "body lumen" may include any passage cavity of the body that conducts fluid, including but not limited to biliary ducts, pancreatic ducts, ureteral passages, esophagus, and blood vessels such as those of the human vasculature system.

As used herein, the term "implantable" may refer to an ability of a medical device to be positioned at a location within a body, such as within a body lumen. Furthermore, the terms "implantation" and "implanted" refer to the positioning of a medical device at a location within a body, such as within a body lumen.

As used herein, "endolumenal," "intraluminal," or "transluminal," may refer to implantation placement by procedures wherein the medical device is advanced within and through the body lumen from a remote location to a target site within the body lumen. Endolumenal delivery may include implantation in a biliary duct from an endoscope or catheter.

As used herein, the term "expandable mesh" may include self-expanding and non-self-expanding configurations made of any generally rigid or flexible material which when expanded have an open network or arrangement which would otherwise allow tissue in-growth, and would not otherwise prevent fluid flow through its walls.

As used herein, the term "tissue adhesive" may include any surface comprising a hierarchical micro pattern which in contact with a target surface resists translation either in a direction orthogonal to the target surface or parallel to a target surface.

As used herein, the term "cell promoter" may include any surface that directs cells in a particular direction, or promotes a certain type of cell to populate a surface, or directs a certain combination of cells to populate a surface, or promotes certain cell types while blocking other cell types.

As used herein, the term "anti-fouling surface" may include any surface that resists the accumulation of a molecule, a particulate, or a cell. An anti-fouling surface generally means a surface which inhibits the accumulation of matter from the environment in which the surface is placed.

As used herein, the term "Wenzel interface" may include any surface with surface texture which when placed in contact with a wet surface draws water in between the surface features of the surface texture.

As used herein, the term "Cassie interface" may include any surface with surface texture which when placed in contact with a wet surface prevents water from interpenetrating between the surface features of the surface texture.

As used herein, the term "eigenmode", "wrinkle eigenmode" and "wrinkle mode" may include any natural wrinkling of a tissue surface when exposed to a shear force.

As used herein, the terms "Schallamach wave" and/or "Schallamach wrinkle" may include any occurrence of waves of detachment known to occur during abrasion experiments with target substrates. Schallamach waves are explained in terms of the elastic instability of the elastomeric surface. If a surface of a device is designed to anticipate these waves by employing a periodic surface structure which is slightly lower in spatial frequency than the anticipated Schallamach wave, then the Schallamach wave will catch in the periodic structure and dramatically increase the shear force required for translation. Such a "Schallamach-matching" design reduces abrasive damage between the device surface and target surface.

The phrases "connected to," "coupled to," and "in communication" may refer to any form of interaction between two or more entities, including but not limited to, mechanical, electrical, chemical, magnetic, electromagnetic, fluid, and thermal interaction. Two components may be coupled to each other even though they are not in direct contact with each other. For example, two components may be coupled to each other through an intermediate component.

While the subject matter of the present disclosure may be embodied in many different forms, there are described in detail herein specific preferred embodiments of the present disclosure. This description is an exemplification of the principles of the present disclosure and is not intended to limit the present disclosure to the particular embodiments illustrated.

For the purposes of this disclosure, like reference numerals in the figures shall refer to like features unless otherwise indicated.

Various medical devices for implantation in a body lumen are disclosed herein. Preferred embodiments relate to a medical drainage device. In general, drainage devices, such as biliary stents, may be implanted to treat various conditions. For example, drainage stents configured as biliary stents may be implanted in the biliary tract to treat obstructive jaundice. FIG. 1 is illustrative of a typical biliary system 100 showing: a right hepatic duct 102 joining with the left hepatic duct 104 to form a common hepatic duct 106; a gallbladder 108 and a cystic duct 110; a pancreas 112 and a pancreatic duct 114; and all aforementioned ducts connecting to form a common bile duct 116 leading to a duodenum 118 through the Papilla of Vater and Sphincter of Oddi 120.

In one embodiment, a biliary stent comprising a tubular member may include two or more planar curvilinear bends. Each bend may be curved in opposite directions with respect to adjacent bends. For instance, a pair of consecutive planar curvilinear bends may form an "S"-shaped or sinusoidal configuration. Additionally, the curvilinear bends may define a tortuous portion of the drainage lumen within the tubular member. The medical drainage devices of the application may describe with respect to an exemplary biliary stent an embodiment comprising a tubular support member.

However, the embodiments of biliary drainage stents may also illustrate other drainage devices, such as ureteral stents, esophageal stents, vascular stents, or drainage catheters provided in accordance with other embodiments.

The present disclosure may also relate to micropatterned polymeric coatings or micropatterned surfaces for use on medical devices. In some embodiments, the micropatterned polymeric coatings or surfaces are utilized with implantable medical devices, such as stents, to reduce or prevent stent migration, particularly for stents used in the gastroesophageal system. These devices may include, but are not limited to, esophageal, biliary, and colonic stents. In one or more embodiments, the micropatterned polymeric coating may include regularly or irregularly spaced, and/or regularly or irregularly shaped, micro-scale textures (e.g., voids, spaces, channels, passages, etc.) that may promote, for example, controlled cell migration and tissue ingrowth.

It is known in the prior art that some tracheal stents have incorporated bumps or other surface features into the stent itself or have included a plurality of surface protrusions on the outer surface of the stent. Surface textures have not been used in the gastrointestinal tract due to the highly lubricated environment. However, the surface textures of the present specification employ the lubrication aspect of gastrointestinal lumen to achieve stent anchoring with a surface texture that creates Wenzel-Cassie zones of interface between the stent and the body lumen.

Ingrowth of tissue into the micropatterned polymeric coatings (e.g., into the textures) may reduce stent migration by anchoring the stent to a body lumen wall (e.g., via controlled cell ingrowth, etc.). In one or more embodiments, the micropatterned polymeric coating may include and/or be formed from a biodegradable material, which may allow, for example, atraumatic stent removal in one or more applications.

In one embodiment, a stent may comprise a region of immediate adhesion to a target lumen when implanted into a body lumen, and a second region designed to promote or direct a particular type of healing tissue ingrowth. Such a dual functional stent is particularly useful in stenting applications where the body lumen is both constricted and damaged.

Figure 2:
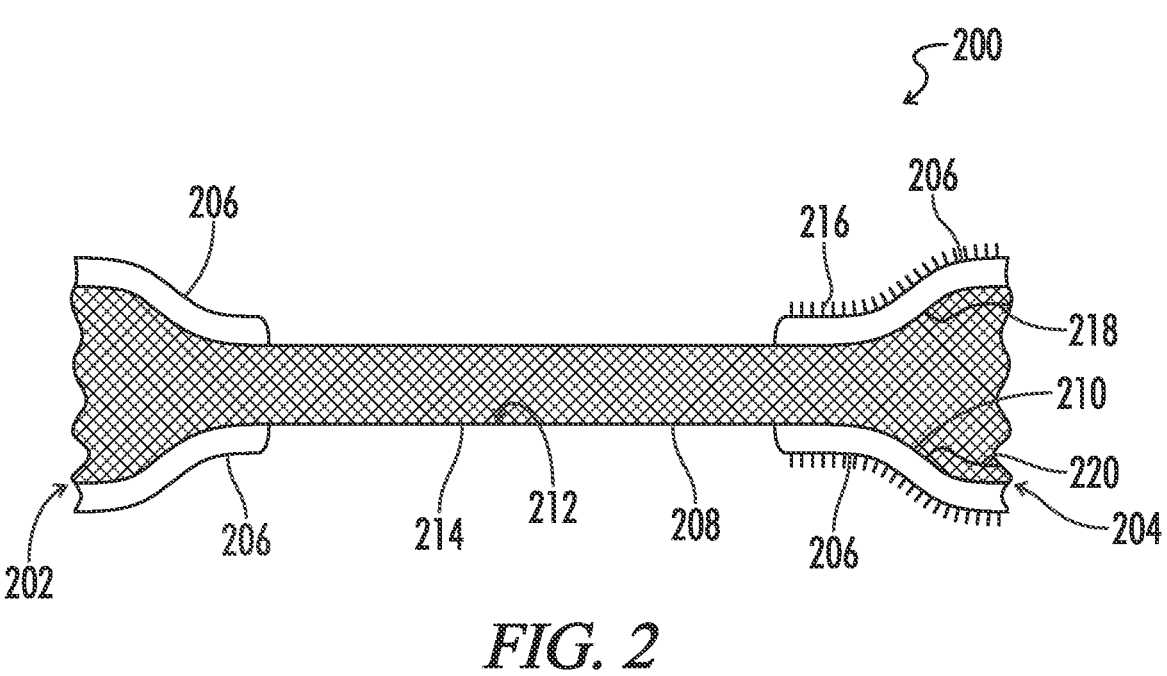
FIG. 2 is a gastrointestinal endoprosthesis, stent, of the present disclosure.

FIG. 2 shows a gastrointestinal stent 200 of the present disclosure with a proximal end 202 and a distal end 204. The stent 200 may include a polymeric coating 206. In one or more embodiments, stent 200 may be a preformed stent. Some embodiments of the stent 200 contemplate having a body 208 with constant diameter, one or more tapers or flares 210 and/or other changes in diameter in the body and/or at one or more ends.

The stent 200 may include an inner surface 212, and an outer surface 214. The polymeric coating 206 may be disposed on at least a portion of the outer surface 214. The copolymeric coating 206 may include a hierarchical pattern 216 on the outer surface of the copolymeric coating. In at least one embodiment, the polymeric coating 206 may substantially cover the entire outer surface 214 of the stent 200. In some embodiments, the polymeric coating 206 may cover only a portion of the outer surface 214 of the stent 200. In one embodiment, the polymeric coating may cover at least 60% of the outer surface 214 area. In some embodiments it may cover at least 80%, at least 90%, at least 95%, at least 99% of the area of the outer surface 214. In some embodiments, the polymeric coating 206 may cover a portion of the outer surface 214 of the stent 200 in concentric rings spaced apart with a spatial frequency as a multiple of a peristaltic frequency, known as a slip-stick pattern placement.

As shown in FIG. 2, the polymeric coating 206 may be disposed about the outer surface 214 of the stent 200. In one or more embodiments, the polymeric coating 206 may be disposed about the outer surface 214 of the stent 200 using an adhesive or other means of attaching the coating to the device. In at least one embodiment, the polymeric coating may also at least partially cover the inner surface 212 at location 218. The polymeric coating 206 may include a hierarchical pattern 216 that is the same pattern at both the outer surface 214 and inner surface 212. Additionally, the polymeric coating 206 may include a hierarchical pattern 216 on the outer surface 214 and a different hierarchical pattern 220 on the inner surface 212. In one embodiment, the polymeric coating may cover at least 60% of the inner surface 212 area. In some embodiments it may cover at least 80%, at least 90%, at least 95%, at least 99% of the area of the inner surface 212.

In at least one embodiment, partial coverage may include partial coverage of the proximal 202 end, the distal 204 end, the body 208, and/or any combination thereof. The polymeric coating 206 may be disposed along the entire stent length, may be incorporated into a silicone coating (e.g., in a patchwork), may be applied to another coating, may be disposed on one or more stent flares 210, and/or helically wrapped around the body 208 of the stent.

Figure 3:
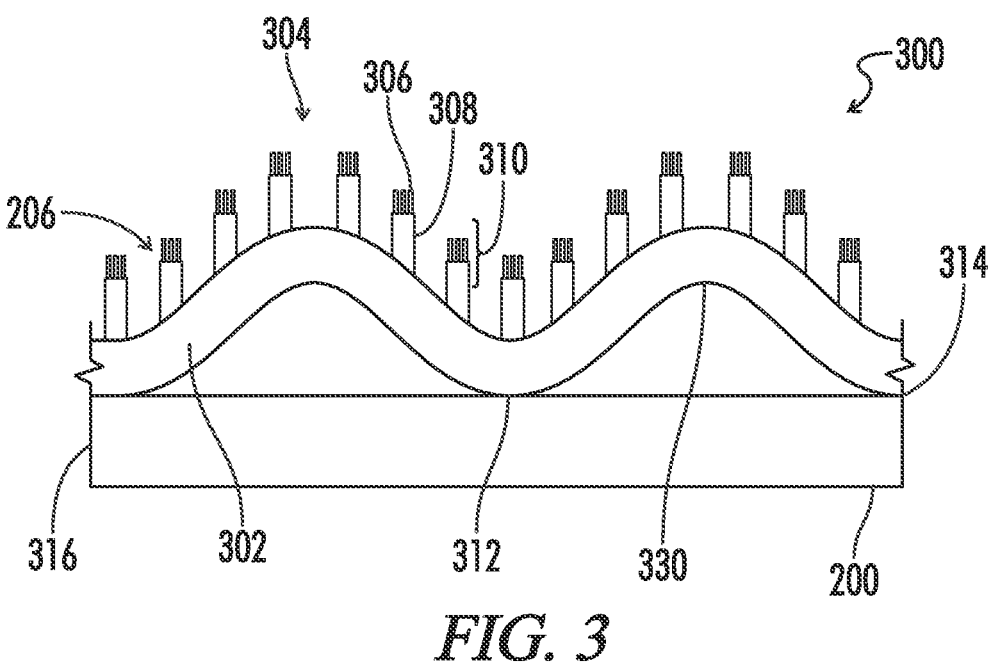
FIG. 3 is an anti-migration coating on a stent of the present disclosure.

In at least one embodiment, shown in FIG. 3, the anti-migration coating 300 may comprise a polymeric coating 206 which may include a base 302 and a plurality of protrusions 304. The plurality of protrusions may include small micro pillars 306 disposed on large micro pillars 308 in a hierarchical arrangement 310, extending outwardly from the base 302. In at least one embodiment, the hierarchical arrangement of micro pillars 310 may be incorporated (e.g., seamlessly incorporated, etc.) into the base 302 of the coating 206. In at least one embodiment, the base portion 312 is coterminous 314 with the stent 200. A person of skill in the art would understand that "coterminous" may refer to the base portion 312 of the polymeric coating 206 and end of the stent 200 having the same boundaries, cover the same area, or are the same in extent. In other words, the stent 200 and the base portion 312 each have first 314 and second ends 316, and the stent 200 and the base portion 312 extend between their first 314 and second ends 316. The first end 314 of the stent 200 is the same as first end of the base portion 312, and the second end 316 of the stent 200 is the same as the second end of the base portion 312. Since the stent 200 and the base portion 312 extend between their first and second ends 314, 316, the stent 200 and the base portion 312 have the same boundaries, cover the same area, and are the same in extent. Thus, the base portion 312 and the stent 200 are coterminous. In addition, base 312 may also be tubular in at least one embodiment.

Figure 4:
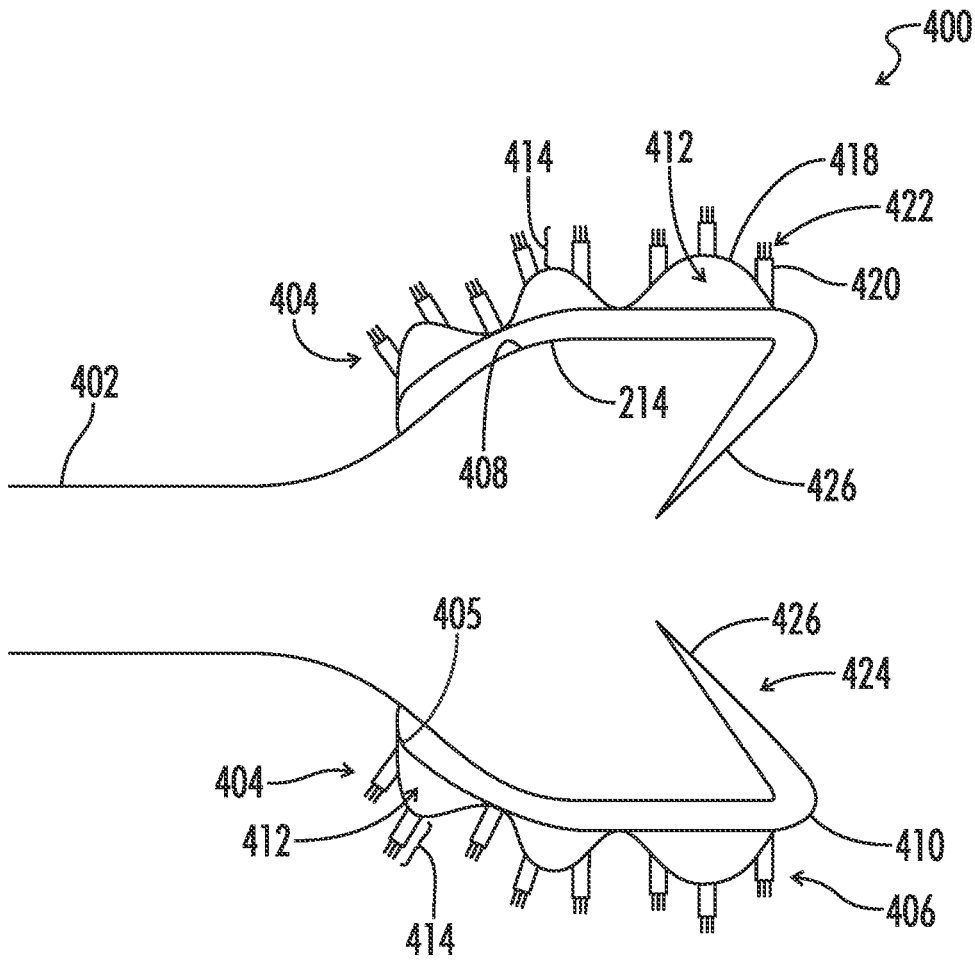
FIG. 4 is an anti-migration coating with a valving mechanism on a stent of the present invention.

Referring now to FIG. 4, a stent end portion 400 may comprise a stent 402, and a polymeric coating 404. The polymeric coating may further include a base 405 and tissue engagement portion 406. Base 405 may include a first surface 408 attached to the outer surface 214 of the stent 400. Methods of attachment may include any method of adhering, bonding, fixing, pasting, or the like. Tissue engagement portion 406 may include a second polymeric surface 410 facing outwardly from the stent 400. The second surface 410 may define a plurality of microstructures 412 from which textures 414 may extend. The tissue engagement portion 406 may include structure 412 defining a plurality of textures such as a first sinusoidal texture 418, a second large pillar texture 420, and a third small pillar texture 422 all arranged hierarchically, extending outwardly from the second surface 410 of the tissue engagement portion 406 away from base 405.

In at least one embodiment, the tissue engagement portion 406 may be seamlessly incorporated into the base 405 of the coating 404. In at least one embodiment, the base 405 may be coterminous with the stent 402. The microstructures 412 may be arranged in a hierarchical micropattern, which may include regularly shaped textures and/or irregularly shaped textures, and which may include textures 418, 420, 422 arranged in a regular pattern and/or in an irregular micropattern. In one or more embodiments, the base 405 covers the apertures 424 of the stent 402 creating a valving mechanism 426.

Figure 5:
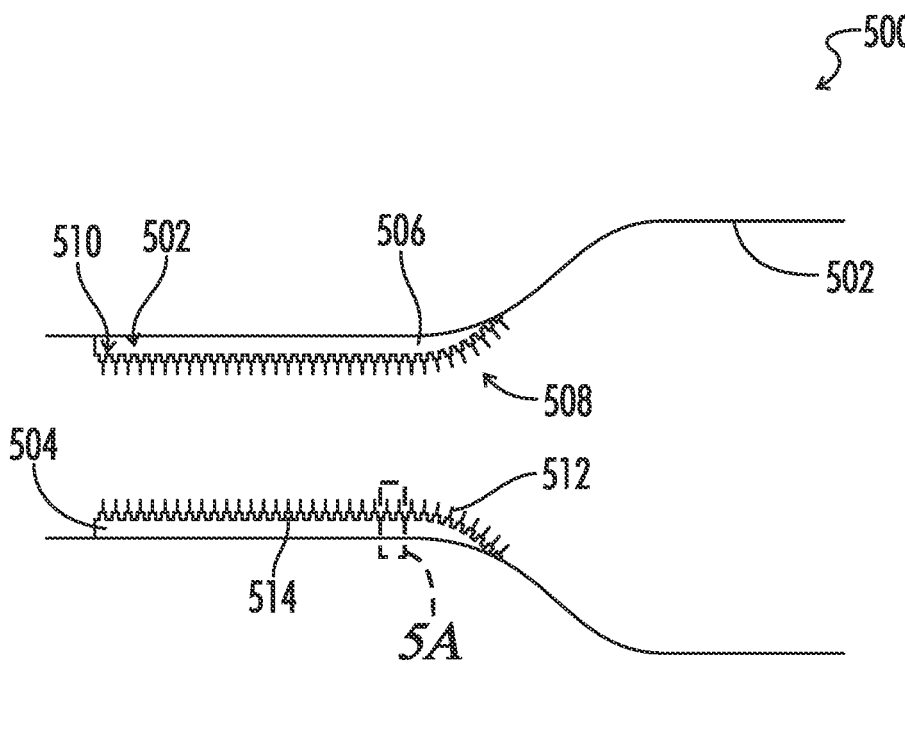
FIG. 5 is an anti-fouling coating on a stent of the present disclosure.
Figure 5A:
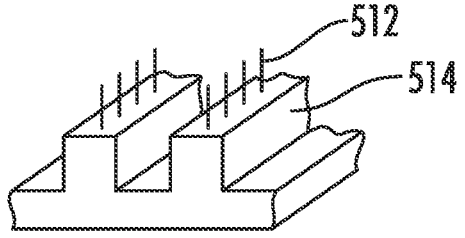
FIG. 5a is a close-up view of the microstructure of the coating of FIG. 5.

Referring now to FIG. 5, a stent with an anti-fouling coating 500 may comprise an internal surface 502. The stent 500 may comprise a polymeric coating 504 which may include a base 506 and anti-fouling surface 508. Base 506 may include a first surface 510 attached to the inner surface 502 of the stent 500. Again, methods of attachment may include any method of adhering, bonding, fixing, pasting, or the like. Anti-fouling coating 504 may include an anti-fouling surface 508 facing inwardly from the stent 500. Internal polymeric coating 504 disposed on internal surface 502 may comprise a plurality of micropillars 512 disposed on top of micro ridges 514 (as shown in FIG. 5a).

In some embodiments, a network of textures may be formed wherein cells are encouraged or alternatively discouraged to migrate into a region. Typically, when a lumen is damaged or compromised by disease it may be beneficial to promote cellular infiltration at the compromised zone to promote healing of the damaged lumen. It may, however, not be desirable to have the in-growth tissue adhere to the stent. A network of textures on a biliary stent may be useful in that the coating may allow and/or promote tissue growth while also maintaining the stent's relatively low profile (relative to a stent having additional scaffolding on the outside of the stent for tissue ingrowth and reducing stent migration) while reducing or preventing re-occlusion of the lumen. A cell growth promoting surface texture, disposed on the outer surface 214 of a stent 200 may be different from an anti-fouling surface 508 or a stent anti-migration (anchoring) surface 300.

Figure 6:
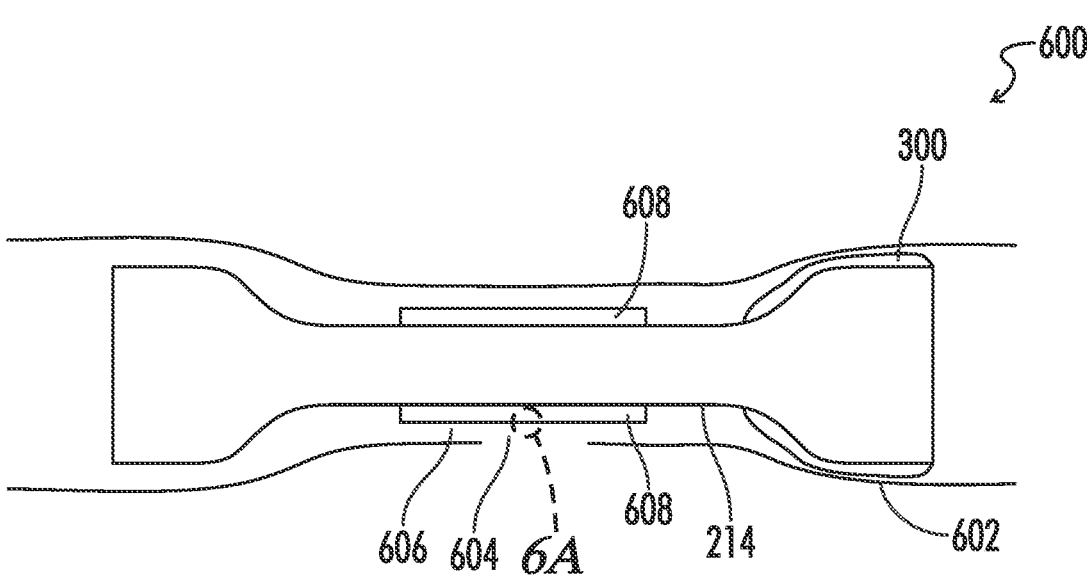
FIG. 6 is a cell promotion coating on a stent of the present disclosure.
Figure 6A:
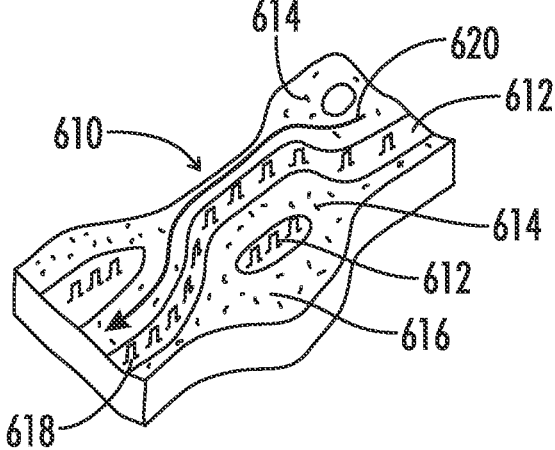
FIG. 6a is a close-up view of the coating of FIG. 6.

Referring to FIG. 6, a stent 600 may include an anchoring and cell directing surface which may be deployed in a body lumen 602 with a tissue defect 604. The outer surface 214 may be disposed at a location 606 where healing is advantageous. A coating 608 may be disposed about the outer surface 214 to promote endothelial cell growth. A coating texture 610 may be a surface comprised of hydrophilic microstructure 612 and hydrophobic microstructure 614 (as shown in FIG. 6a). Structures 612 and 614 may be hierarchical. The spacing 616 of texture 614 and spacing 618 of texture 612 may be chosen to match or not match a cellular dimension, such that cells can migrate in a preferred direction 620. A gradient of surface energy (spacing of microstructures) may further promote cellular mobility.

Additionally, structures 612 and 614 may be adapted to allow controlled cell ingrowth at an implantation site and allow atraumatic removal of the stent (e.g., before, during, and/or after cell ingrowth occurs). In particular, structures 612 and 614 may promote cellular migration but may not promote cellular ingrowth into the stent. Such migrating cells will associate with the compromised section of the body lumen and may begin organized tissue construction and lumen repair.

In one or more embodiments, one or more textures may extend completely through the thickness of the coating. In one or more embodiments, one or more of the textures may be a blind texture (e.g., a cavity, an indentation, a texture having a bottom, a texture that does not extend from the second surface to the first surface).

In some embodiments as shown in FIGS. 2-6, the micropillars are cylinders, prisms with a rectangular or polygonal base, pyramids, or bumps, or any combination thereof, and may be arranged in combination hierarchically. Hierarchical arrangement may result in an overall texture which is compound and non-traditional in shape with a plurality of protuberances, valleys, and ridges on multiple surfaces that do not define a cross-section that is circular, square, polygonal, or the like. Individually, the textures may be micropillars with, for example, a circular cross-section, square cross-section, rectangular cross-section, star-shaped cross-section, hexagonal cross-section, pentagonal cross-section, heptagonal, octagonal cross-section, nonagonal cross-section, decagonal cross-section, other polygonal cross-sections, or non-traditional shaped cross-sections. Some embodiments may comprise a surface texture of a single type of micropillar cross-section, or may comprise a surface texture of any combination of the aforementioned micropillar cross-sections.

Each structure type has a cross-section with a first dimension "h" that is the greatest distance between the outer surface of the base and the end of the structure, and a second dimension "d" that is the greatest distance between two opposite sides (e.g., of a pillar). For example, for the circular cross-section the second dimension "d" is the diameter, for the square cross-section the second dimension "d" is between two opposing sides, for the rectangle, the dimension is between the two shorter sides, for the star, the dimension is between two points, for the hexagon the dimension is between two opposite points. In some embodiments, the second dimension "d" is between midpoints of two opposite sides. In at least one embodiment, a cross section of the micropillar taken in the radial direction has at least four sides.

Embodiments of the present disclosure contemplate polygonal cross-sections having all sides of equal length, combinations of sides of equal length and unequal length, or all sides of unequal length. Embodiments of the present disclosure contemplate multiple pillars of multiple cross-sectional shapes including traditional shapes (e.g. circles, squares, rectangles, hexagons, polygons, etc.) and non-traditional shapes having a perimeter where at least a portion of the perimeter is curvilinear. In at least one embodiment, the micropillars are solid structures, but in other embodiments they can be hollow structures. In at least one embodiment, each micropillar has a constant cross-section, but in other embodiments the micropillars have variable cross-sections. In at least one embodiment, micropillars extend perpendicularly from the base. In at least one embodiment, micropillars extend from a base in a non-perpendicular angle wherein the geometric center of the end of the micropillar is offset laterally from the geometric center of the area of the base covered by the micropillar. For example, a longitudinal axis of the micropillars extending through the geometric centers of the lateral cross-sections forms an angle that is less than 90 degrees with the base. In at least one embodiment, the plurality of micropillars can be arranged in a hierarchical arrangement in one or more particular micropatterns.

In one or more embodiments, textures may take any of the shapes and dimensions described herein regarding micropillars. In general, in a hierarchical arrangement there is a base structure that may be flat, continuously varying as in a sinusoidal profile, stepped as in an ascending and descending staircase, perforated, or otherwise varied in a random or regular pattern, the features of which may be characterized by a dimensional measure or a range of a dimensional measure. For example, in a sinusoidal profile in two dimensions, the pattern may be characterized by a wavelength or range of wavelengths. One aspect of the present invention is that a second set of textures may be disposed on top of this base. The second texture may be pillars, ridges, pyramids, and the like, as listed previously. This second set of textures may also have characteristic dimensional measures, which may include pitch, height, diameter, and the like. In some embodiments, the dimensional measure of the base may be larger than the dimensional measure of the second set of textures. In such an embodiment, the ratio between first and second dimensional measures is between 1:10 and 1:0.5. In one embodiment there may be a third set of textures disposed on the second set of textures, and optionally disposed on the first set of textures located between the structures of the second set of textures. Depending on the desired effect, the ratio between these dimensional measures may be selected. For example, for a stent device with anti-fouling properties, the pitch relative to the height of the textures may be small. In some embodiments, the height may be 1 to 10 times the pitch. A high height to pitch ratio may make a hydrophobic surface, with low surface energy. Low surface energy structures resist deposition of the typically ionic moieties found in biological tissue. If the desired effect is to promote cellular migration along a surface, then the structure dimensions may be chosen to generate a surface energy gradient, with structures dimensioned and positioned such that cells may readily bridge and travel along the structures. Surfaces with deep valleys may discourage cell migration. Cells depend on a continuity of attachment sites in order to propagate along a surface. A combination of tall pillars spaced closely, such that cells do not readily fit between them, may have the desired effect of promoting cellular propagation across a surface without the cells growing into the surface. Cellular ingrowth into a stent surface may be discouraged such that cells are directed to repairing a tissue defect without making stent removal difficult. Additionally, a stent may also be textured so as to resist migration (or to anchor). Migration resistant surface textures are typically Wenzel-Cassie textures. Such surface textures may create zones of hydrophilic attraction and hydrophilic repulsion, such zones when interlocking resist migration of the stent within the body lumen.

Referring back to FIG. 3, anti-migration coating 300 comprising textures 306, 308 and 330 may take the shape of a prism having a cross-section defined by any of the shapes described above. In one or more embodiments, the shape of textures 306, 308 and 330 may be randomly selected from a cylinder, a rectangular prism, a prism with a polygonal base, a sphere, a spheroid, and an ellipsoid. The texture structure may define textures 306, 308 and 330 having the same shapes repeated in a regular array. The height and pitch of the textures 306, 308 and 330 may be any height and pitch up to but no greater than the thickness of the polymeric coating 300 (e.g., the sum of thickness of the base 318 and the tissue engagement portion 310). In one or more embodiments, the base may be continuous and devoid of textures extending therethrough. In one or more embodiments, the base 318 may include a base structure that defines a plurality of base textures 330 (e.g., which may be in fluid communication with the plurality of textures 306 and 308 of the tissue engagement portion 310). These base textures may extend over the region where the tissue engagement structures 310 reside, so as to create a hierarchical structure. FIG. 3 illustrates a hierarchical structure, structure 306 may be disposed upon structure 308, and structure 308 may be disposed upon structure 330.

Although not wishing to be bound by theory, the micropattern dimensions may affect the conformability of the micropattern to an irregular target surface. For example, the base microstructure 330 of FIG. 3 could result from laying a flat base 318 on a periodic structure formed by the woven structure of a wire stent. For example, a low durometer polymer coating may naturally be directed inward in the regions where the polymeric coating bridges the open spaces between wires.

In some embodiments, a stent of the present invention may be a wire woven stent, where the spatial periodicity of the wires comprising the stent match some eigenmode of the target tissue, either a flexural eigenmode or a peristaltic eigen mode, or both. When the eigenmodes are excited by placement of the stent, then an anti-migration coating may deform naturally to engage these target eigenmodes. When the stent structure is such that it induces a target microstructure in the polymer coating, then the coating may be made thinner and enable the stent to deploy more easily when expanded.

Figure 7:
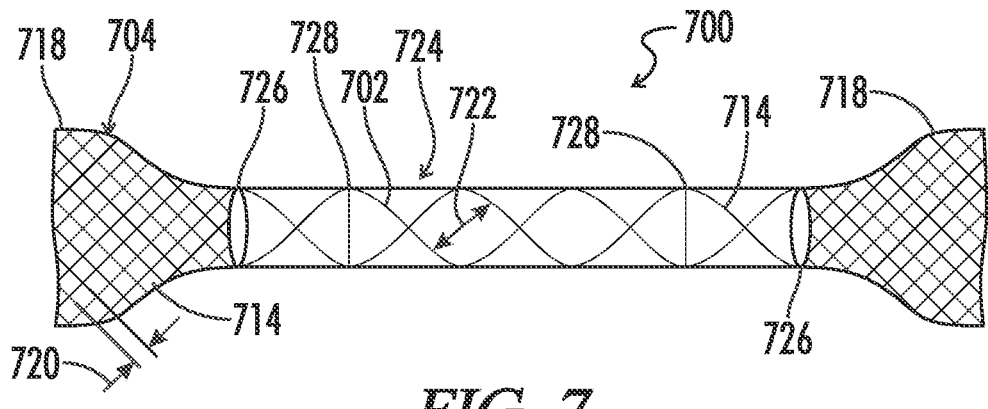
FIG. 7 is a stent with anti-migration surface texture in one region which conforms to a tissue eigenmode spatial frequency, and another region which conforms to a peristaltic spatial frequency.
Figure 7A:
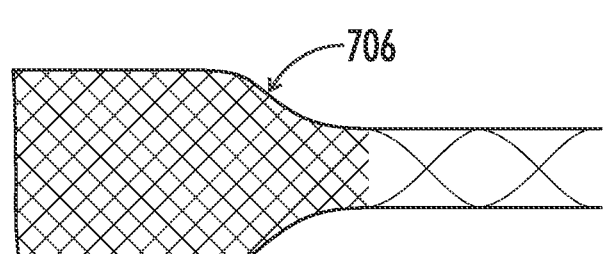
FIG. 7a is a close-up view of one end of the stent of FIG. 7 showing compression.
Figure 7B:
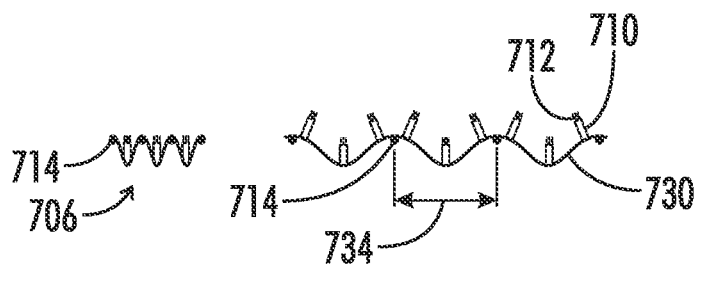
FIG. 7b is a depiction of the wire spacing of the stent of FIG. 7.
Figure 7C:
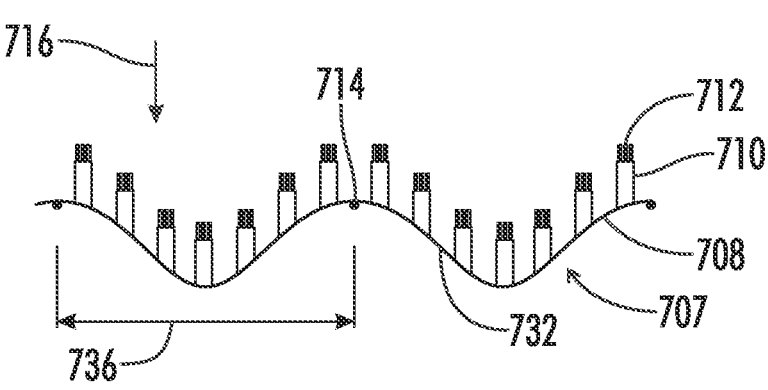
FIG. 7c is another depiction of a different wire spacing of the stent of FIG. 7

Referring to FIG. 7, a stent 700 with part of the microstructure formed by the stent structure is illustrated. A stent 700 may be comprised of wire 702 deployed in form 704 and compressed in form 706 (shown in FIG. 7a). The stent 700 may also include an anti-migration coating 707, which may be comprised of a flat base 708, first pillars 710, and second pillars 712. Flat base 708 may be attached to stent wires 714. When the stent 700 is deployed, an inward directed force 716 may deform flat base 708 into a sinusoidal pattern (as shown in FIG. 7c) first level of the microstructure. The stent 700 may be comprised of flared regions 718 where the wire spacing 720 is closer than the wire spacing 722 in the body region 724. The anti-migration coating 707 in the flared regions 718 may stop at the transition location 726 where the body 724 transitions to the flared regions at each end. In other embodiments, the surface coating may extend beyond this transition location 726, but optionally may do so without surface textures 710 and 712. The anti-migration coating 707 in the body region 724 may be delimited by markings 728. The spacing 730 between pillars 710 in the flared region 718 may be different from the spacing 732 between pillars 710 in the body region 724. The wire spacing in the flared region 718 in the deployed position 704 is represented by wire spacing 734. The wire spacing in the body region 724 in the deployed position 704 is represented by wire spacing 736. Wire spacing 734 may be matched to a flexure eigenmode spatial frequency of the body lumen (as shown in FIG. 7b). The wire spacing 736 may be matched to a peristaltic spatial frequency (as shown in FIG. 7c). The wire spacing 734 may be matched to a flexure eigenmode spatial frequency of the body lumen in the flared regions 718 so that the stent is may forcefully contact the body lumen at the flared positions 718 so as to reduce migration. In one embodiment, the stent body region 724 may follow the peristaltic motion without losing grip.

In general, contact between a surface texture and a target lumen surface may be desirable. In some embodiments, a gap between the surface texture and target surface may be less than approximately 2 times the height of the largest surface texture's height. In this environment between the surface texture and target lumen surface, there may be a fluidic or gaseous gap between where the adhesion of the micropattern is not dependent upon frictional engagement or any interlocking mechanism between the micro features (e.g., micropillars, textures, etc.) of the endoprosthesis and the tissue. Conversely, if frictional engagement with tissue is desired, such functionality can be added to the surface patterns of the present specification. For this reason, in at least one embodiment, one or more particular microstructures may be selected that has a micropattern geometry and dimensions suitable for a particular application (e.g., anti-fouling, promotion of biological tissue formation, desired anti-migration properties, and the like as previously mentioned and further detailed below).

It is known that cells such as fibroblasts, endothelial cells, and muscle cells actively sense both the external loading applied to them (outside-in signaling) and the stiffness of their surroundings (inside-out signaling). Accordingly, the surface texture of the present invention may be constructed from a polymer with elastomeric properties. Cells may respond to modulus stimuli with changes in adhesion, proliferation, locomotion, morphology, and synthetic profile. Specific structure of micro-scale features (e.g., textures, voids, pores, and the like) as well as coating material properties and surface energy properties may be useful in controlling or promoting cell behavior under certain conditions. The modulation of these properties to suit cellular dimensions may be particularly effective at encouraging some cell types and discouraging other cell types.

In at least one embodiment, the micropillars in the micropattern may all have the same shape, and in other embodiments, the micropillars may vary in shape along the polymeric coating. Thus, in at least one embodiment, the micropattern may include portions where the micropillars have a first configuration and portions where the micropillars may have a second configuration. Some embodiments may include the polymeric coating having only one micropattern or the polymeric coating having multiple micropatterns. Thus, the polymeric coating can be tailored to specific structural characteristics of the body lumen and a desired engagement, cellular promotion, or anti-fouling aspect may be achieved, while using a single stent.

Similarly, in one or more embodiments, textures may be configured and arranged in the same manner described herein for micropillars disposed on a two-dimensionally sinusoidally varying base. That is, in at least one embodiment, the textures in the micropattern may have a discrete shape combined with a continuous shape, and in other embodiments, the textures may vary in shape along the polymeric coating. Thus, in at least one embodiment, the micropattern may include portions where the textures have a first orientation and portions where the textures have a second orientation. Moreover, embodiments include the polymeric coating having only one micropattern (e.g., of random textures, of micropillars, or the like) or the polymeric coating having multiple micropatterns (e.g., two or more different micropatterns of textures, two or more micropatterns of micropillars, one or more micropattern of textures in combination with one or more micropatterns of micropillars, and the like). Thus, the polymeric coating may be tailored to specific structural and/or anatomical characteristics of the body lumen and a desired frictional engagement or interlock can be achieved, all while using a single stent. In one or more embodiments, a micropattern may include one or more textures in combination with one or more micropillars, for example a micropattern including a first number of textures alternating with a second number of micropillars. In one or more embodiments, a polymeric coating may include a micropattern of micropillars and a micropattern of textures, wherein the micropatterns may or may not overlap.

In at least one adhesive embodiment, the dimension measure (e.g., of textures, of micropillars, and the like) is between 1 micron and 100 microns for a first texture, is between 25 and 150 microns for a second texture, and is between 100 microns and 10,000 microns for a third texture, wherein the first texture may be disposed on the top of the second texture, and the first and second textures may be disposed on the top of the third texture. In at least one embodiment, the first-dimension measure may be between about 1 micron and 10 microns, the second-dimension measure may be between 20 microns and 50 microns, and the third-dimension measure may be between 100 microns and 600 microns. In at least one embodiment, the high end of the dimension measure may be equal to the height (e.g., of textures, of micropillars, etc.) and the low end of the dimension measure may be the diameter. In at least one embodiment, a ratio of height to diameter is between about 1:1 and 1:2.5. In at least one embodiment, two adjacent micropillars may be spaced apart by a distance called the pitch. In at least one embodiment, the ratio of the pitch to the diameter is between about 1:2.1 and 1:10.

In at least one anti-fouling embodiment, the dimension measure (e.g., of textures, of micropillars, and the like) may be between 1 micron and 100 microns for a first texture, may be between 25 and 150 microns for a second texture, and may be between 100 microns and 10,000 microns for a third texture, wherein the first texture may be disposed on the top of the second texture, and the first and second textures may be disposed on the top of the third texture. In at least one embodiment, the first-dimension measure may be between about 1 micron and 3 microns, the second-dimension measure may be between 10 microns and 25 microns, and the third-dimension measure may be between 50 microns and 100 microns. In at least one embodiment, the high end of the dimension measure may be equal to the height (e.g., of textures, of micropillars, and the like) and the low end of the dimension measure may be the diameter. In at least one embodiment, a ratio of height to diameter is between about 1:3 and 1:10. In at least one embodiment, two adjacent micropillars may be spaced apart by the pitch. In at least one embodiment, the ratio of the pitch to the diameter is between about 1:2.1 and 1:3.

In at least one cell promoter embodiment, the dimension measure (e.g., of textures, of micropillars, and the like) may be between 1 micron and 100 microns for a first texture, may be between 25 and 150 microns for a second texture, and may be between 100 microns and 10,000 microns for a third texture, wherein the first texture may be disposed on the top of the second texture, and the first and second textures may be disposed on the top of the third texture. In at least one embodiment, the first-dimension measure may be between about 1 micron and 2 microns, the second-dimension measure may be between 20 microns and 50 microns, and the third-dimension measure may be between 1000 microns and 2000 microns. In at least one embodiment, the low end of the dimension measure may be equal to the height (e.g., of textures, of micropillars, and the like) and the high end of the dimension measure is the diameter. In at least one embodiment, a ratio of height to diameter may be between about 1:1 and 1:2.5. In at least one embodiment, two adjacent micropillars may be spaced apart by the pitch. In at least one embodiment, the ratio of the pitch to the diameter is between about 1:2.1 and 1:2.5.

In some embodiments, the ends of the protrusions that are furthest away from the outer surface of the base may be shaped to improve cell attachment. In some embodiments, these protrusions may be micropillars. In one or more embodiments, the ends of the protrusions may be tapered, pointed, rounded, concave, convex, jagged, or frayed, and the like.

In some embodiments, the sides of the protrusions that are furthest away from the outer surface of the base may be shaped to improve cell attachment. In some embodiments, these protrusions may be micropillars. In one or more embodiments, the sides of the protrusions may be fluted, undulating, adorned with axially concentric parallel ridges, adorned with axially parallel ridges, spines, jagged ridges, or frayed spines, and the like.

The second surface of the tissue engagement portion may be adapted to improve tissue attachment. In one or more embodiments, the lateral and/or bottom surfaces of the textures may be tapered, fluted, punctured, concave, convex, jagged, or frayed, and the like. It will be understood that any adaptation such as shaping, texturing, or modifying the tissue engagement portion may be used by one skilled in the art.

In at least one embodiment, the protrusions, such as micropillars, may also include terminal features such as mushroom shaped terminations with involuting curvature, downward pointing spines, a plurality of bumps with concave centers extending outwardly from a surface of the micropillar, in particular the terminal surface, a plurality of indentations extending inwardly from a surface of the micropillar, a plurality of ridges arranged concentrically on a terminal surface of the micropillar, a tip at or near the end of the protrusion that is either softer or more rigid than the remainder of the protrusion, a frayed tip, a convex tip, a flared tip, a concave tip, a tip having a first dimension that is greater than the diameter of the micropillar column extending outward from the base and the tip, and other features that may be coated with a thin layer of material with a specific surface energy, which may be useful in differentiating the surface energy of an adjacent surface such that a Wenzel-Cassie domain may be established which is useful in gripping, improving stiffness, or flexibility characteristics for the interface between the endoprosthesis and tissue, and any combination of features thereof.

In at least one embodiment, the tip of the protrusion may include a different material than the remainder of the protrusion. Similarly, the end and lateral surfaces of textures may be shaped to improve tissue attachment similar to that described above with respect to micropillars. For example, textures may include features such as smooth surfaces, rough surfaces, a plurality of bumps extending outwardly from a surface of the texture to create a capillary action aspect, a plurality of indentations extending inwardly from a surface of the texture, a plurality of ridges on a surface of the texture, a frayed end, a convex top end, a flared bottom end, a concave top end, a bottom having a first dimension that is greater than a characteristic diameter of a protrusion extending between the second surface and the end, and other features that may impact a flow aspect useful in developing a capillary suction aspect for gripping, making stiff the interface between the endoprosthesis and the tissue layer, or improve flexibility characteristics for the endoprosthesis by providing a gliding or flowing aspect on a microscale, and any combination of features thereof.

Figure 8:
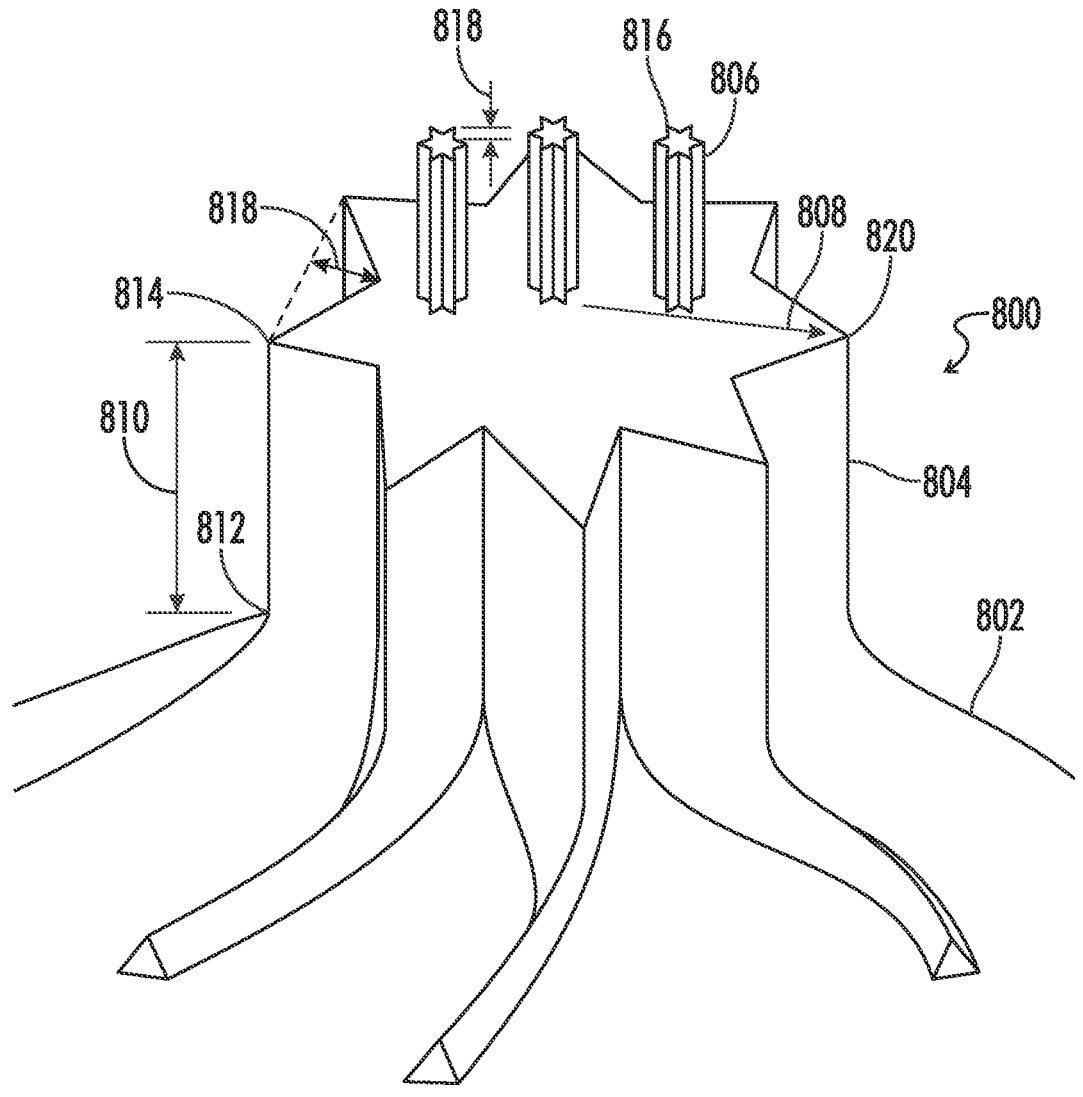
FIG. 8 is an enlarged view of the polymeric coating having hierarchically arranged fluted micropillars.

FIG. 8 depicts an enlarged view of a polymeric coating 800 having hierarchically arranged fluted micropillars. The base structure may include a sinusoid pattern 802. In at least one embodiment, the fluted micropillars may include cylinders 804 and 806. Each of the micropillars may include a diameter (as depicted by annotation 808). Each of the micropillars may also include a height (as depicted by annotation 810). It is to be understood that the annotations on FIG. 8 are for informational purposes only, and that while other micropillars may not include the annotations for diameter 808 and/or height 810, each of the micropillars may be measured in the same manner. The diameter 810 may be measured from an outer surface of the base 812 to the top surface 814 of the cylinder shape comprising the micropillar. In at least one embodiment, the diameter of micropillar cylinders 806 may be between 1 micron and 50 microns with flutes 816 circumferentially distributed about the cylinder. The flute depth 818 (projection from the cylindrical surface) may be between 0.1 microns and 5 microns. In at least one embodiment, the cylinder diameter 808 is between about 1 micron and 5 microns and the flute depth 818 between 0.1 microns and 2 microns. In at least one embodiment, the diameter of the micropillar may be at least equal to its height. In at least one embodiment, a ratio of the height of the micropillar to the diameter of the micropillar may be between about 1:1 and 1:5. In at least one embodiment, the micropillars may each have a lateral surface covered with flutes. The flutes may extend from the pillar surface between 0.1 and 2 microns and are spaced between 1 and 5 microns apart. In at least one embodiment, two adjacent micropillars may be spaced apart. The micropillars may be spaced apart such that a Wenzel-Cassie interface is formed between the region between pillars and between the region between flutes. For example, a Wenzel-Cassie mechanism induced by surface energy differences or van der Waals forces between the fluted region and the region between pillars may be formed.

For tissue ingrowth the micropillars may be spaced apart enough so that the cells of the bodily lumen can fill the negative space (e.g., void space) between the pillars.

The space between protrusions may be between 1 and 3 times the mean diameter of the cells. If the spacing is too small, cell propagation may not occur (e.g., the cells may not be able to form macroscopic tissue). In at least one embodiment, the spacing between the micropillars may be dependent upon, and may be selected based upon, the particular type of cell of the bodily lumen one wishes to promote. For example, promotion of endothelial cells over fibrotic cells encourages functional tissue formation over scar tissue formation. In at least one embodiment, the micropillar pitch may be greater than the diameter of the micropillars. In at least one embodiment, the ratio of the pitch to the diameter may be between about 1:1.5 and 1:3.

For tissue ingrowth, a composite structure may be preferred. In certain regions the micropillars may be spaced apart sufficiently so that endothelial cells are promoted and in other regions the micropillars may be spaced apart sufficiently so that fibrotic cells are provided. In at least one embodiment, the dimensions chosen may be mutually exclusive to the other cell type, such that one spacing promotes endothelial cells and discourage fibrotic cell, and that the other spacing promotes fibrotic cells and discourages endothelial cells. In at least one embodiment, the composite surface texture may be responsible for the generation of macroscopic tissue comprised of fibrotic structural element interwoven with vascular tissue and smooth muscle.

Figure 9:
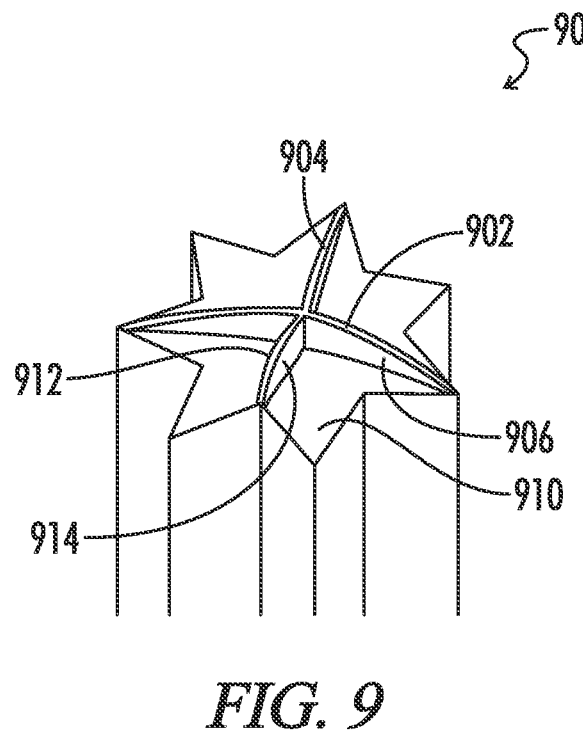
FIG. 9 is an enlarged view of the polymeric coating having a hierarchical ridged surface texture.

FIG. 9 depicts an enlarged view of a polymeric coating 900. In at least one embodiment, the textures may be ridges 902 that each have a diameter 904 and a height 906 measured from the second surface 910 of the tissue engagement portion to a top 912. of the ridge. In at least one embodiment, the diameter 904 may be between 1 micron and 50 microns. In some embodiments the diameter may be between 1 micron and 10 microns, between 1 micron and 5 microns, and between 1 micron and 1.5 microns. In at least one embodiment, the diameter 904 may be between about 1 micron and 2 microns. In at least one embodiment, the diameter 904 of the ridge texture may be at most equal to its height 906. In at least one embodiment, a ratio of height 906 to diameter 904 of the texture may be between about 1:1 and 1:10. In at least one embodiment, the ridge textures 902 may each have a lateral surface 914. In at least one embodiment, two adjacent textures 902 are spaced apart (e.g., spaced apart at the second surface 910 of the tissue engagement portion 900). The micropillars may be spaced apart to encourage cell migration along a line, for example, via an engagement mechanism (e.g., surface energy gradient, van der Waals forces gradient, and the like).

In some embodiments, the textures may be spaced apart so that the cells of the body lumen can propagate along the negative space between two ridges (e.g., void space) within the ridge textures. If the spacing between ridge textures is too large, cellular ingrowth may not be selective. In at least one embodiment, the spacing between the textures may be dependent upon, and may be selected based upon, the particular type of cells comprising the body lumen. In at least one embodiment, the spacing may be measured between the ridge centers of one ridge and an adjacent ridge along the second surface. In at least one embodiment, the ratio of the spacing between adjacent textures to the diameter of the textures is between about 1:1.01 and 1:2.0. In other embodiments, the ratio of spacing may be between about 1:1.01 and 1:1.5.

In at least one embodiment, the microridges and/or textures may be spaced apart equidistantly in the micropattern in a first set of regions of the base and spaced apart equidistantly of a different distance in the micropattern in a second set of regions of the base. In at least one embodiment, the micropattern of ridges may be a curvilinear array. In at least one embodiment, the micropattern of a first curvilinear array of ridges intersects at an angle with a second curvilinear array of ridges to form a grid pattern. This may take the form of a square array. In at least one embodiment, the micropattern of ridges may be a regular n-polygonal array (e.g., hexagonal array), wherein a micropillar or texture may be present in the center of the ridges forming polygons or may not be present in the center of a polygon in the center of the ridges forming polygons. In other words, in the micropattern, the micropillars and/or textures may be arranged in an array in the micropattern of the ridges, wherein the rows and columns of the array may or may not be perpendicular.

In one or more embodiments, each micropillar or texture may include a longitudinal axis and the micropillars are axially aligned in at least one of the axial directions (e.g., arranged in a row parallel to a longitudinal axis of a stent) and the circumferential direction of the endoprosthesis (e.g., arranged in a row extending circumferentially around a longitudinal axis of a stent). In at least one embodiment, the micropattern of micropillars or textures may include any or all of the features described in the previous paragraph.

In some embodiments the micropattern may cover only a portion of the base rather than the entire base. The micropattern of micropillars or textures may be helically disposed on the base. In one or more embodiments, a first micropattern may be disposed longitudinally along the base and a second micropattern may be disposed circumferentially about the base so that the micropattern forms a tessellation-like configuration. Micropillars may be arranged in a row (e.g., parallel to a longitudinal axis of a stent) which may be continuous rows or discontinuous rows (e.g., aligned row segments separated by a gap), wherein the length of the discontinuity may have any length. Discontinuous rows (and circumferentially oriented columns) can extend across the tessellations wherein the length of the discontinuity is five times the separation distance.

Regarding the material used for the polymeric coating, it may be useful for the material to be flexible and/or elastic so as to create a malleable contact with the tissue, be able to withstand the processing for creating the polymeric coating, and to accommodate stent mechanics such as elongation and conformability to tortuous anatomy. Examples of malleable materials include, but are not limited to, flexible silicones, polyurethanes, hydrogels, mucoadhesive substrate, pressure-sensitive adhesives, and the like, and other suitable elastomers, such as synthetic rubbers. Stiffer substrates can be used in discrete configurations. Examples of stiff materials include, but are not limited to, polypropylene, polylactic acid polymer, PEEK, and polyacrylics, and the like.

In one or more embodiments, a coating having a micropattern may include and/or be formed from a biologically-derived protein structure. Other acceptable materials include any flexible, biocompatible, and/or non-biodegradable polymer. For palliative treatment stent applications, it may be useful for the coating to include one or more non-biodegradable polymers and/or a material having a degradation profile that may be useful for the particular stent application and implantation site. In one or more embodiments, the coating may be biodegradable in order to allow stent removal. In one embodiment, stent removal may occur after some portion or all of the coating has degraded. Applications in which it may be useful to remove a stent may include support during perforation healing, dilatation of benign structures, and bridge to surgery.

Biodegradable polymers that may be used to form the support frame of a medical device, or can be coated on a frame, include a wide variety of materials. Examples of such materials include but are not limited to, polyesters, polylactides, polycarbonates, polyanhydrides, poly(amino acids), polyimines, polyphosphazenes and various naturally occurring biomolecular polymers, as well as co-polymers and derivatives thereof. Certain hydrogels, which are cross-linked polymers, can also be made to be biodegradable. These include, but are not necessarily limited to, polyesters, pluronans, poly(amino acids), copoly(ether-esters), polyalkylenes oxalates, polyamides, poly(imino carbonate), poly-orthoesters, polyoxaesters, polyamidoesters, polyoxaesters containing amido groups, polyanhydrides, polyphosphazenes, poly-alpha-hydroxy acids, trimethylene carbonate, poly-beta-hydroxy acids, polyorganophosphazines, polyanhydrides, polyesteramides, polyethylene oxide, polyesterethers, polyphosphoester, polyphosphoester urethane, cyanoacrylates, poly(trimethylene carbonate), poly(imino carbonate), polyalkylene oxalates, polyvinylpyrrolidone, polyvinyl alcohol, poly-N-(2-hydroxypropyl)-methacrylamide, polyglycols, aliphatic polyesters, poly(orthoesters), poly(ester-amides), poly anhydrides, modified polysaccharides and modified proteins. Some specific examples of bioabsorbable materials include poly(epsilon-caprolactone), poly (dimethyl glycolic acid), poly(hydroxybutyrate), poly(p-dioxanone), polydioxanone, PEO/PLA, poly(lactide-co-glycolide), poly(hydroxybutyrate-co valerate), poly(glycolic acid-eo-trimethylene carbonate), poly(epsilon-caprolactone-co-p-dioxanone), poly-L'Glutamic acid or poly-L-Ly sine, polylactic acid, polylactide, polyglycolic acid, polyglycolide, poly(D,L-lactic acid), L-polylactic acid, poly(glycolic acid), polyhydroxyvalerate, cellulose, chitin, dextran, fibrin, casein, fibrinogen, starch, collagen, hyaluronic acid, hydroxyethyl starch, and gelatin.

In at least one embodiment, the polymeric coating may include polymerized hyaluronans capable of conforming to a lumen wall in a biochemical manner. Hyaluronans coupled with surface patterns may be especially effective as tissue promoters. In one or more embodiments, the polymeric coating may comprise one or more growth factors that promote cell migration and/or control the amount and timing of cell invasion/tissue ingrowth between textures and/or within the hierarchical structure of textures. It is important to recognize in constructing tissue promoting surface textures that consideration be given to selection and direction of cell types, and to directing these cell types together to make a healing macroscopic tissue.

In at least one embodiment, the polymeric coating may comprise at least one therapeutic agent. In other embodiments, an additional coating may be applied to the polymeric coating that comprises a therapeutic agent. A therapeutic agent may be a drug or other pharmaceutical product such as non-genetic agents, genetic agents, cellular material, protein removed extracellular matrix, and the like. Some examples of suitable non-genetic therapeutic agents include but are not limited to anti-thrombogenic agents such as heparin, heparin derivatives, vascular cell growth promoters, growth factor inhibitors, paclitaxel, and the like. Where an agent includes a genetic therapeutic agent, such a genetic agent may include but is not limited to DNA, RNA, and their respective derivatives and/or components, especially where such genetic derivatives are bonded to a polymeric surface. Therapeutic agents include cellular material, which may include but is not limited to cells of human origin and/or non-human origin as well as their respective components and/or derivatives thereof. In one or more embodiments, a suitable therapeutic agent may include small organic molecules, peptides, oligopeptides, proteins, nucleic acids, oligonucleotides, genetic therapeutic agents, non-genetic therapeutic agents, vectors for delivery of genetic therapeutic agents, cells, therapeutic agents identified as candidates for vascular treatment regimens, and the like.

In some embodiments, a stent may be treated with a therapeutic agent or agents. "Therapeutic agents", "pharmaceuticals," "pharmaceutically active agents", "drugs" and other related terms may be used interchangeably herein and include genetic therapeutic agents, non-genetic therapeutic agents, and cells. Therapeutic agents may be used singly or in combination. A wide variety of therapeutic agents may be employed in conjunction with the present invention including those used for the treatment of a wide variety of diseases and conditions (i.e., the prevention of a disease or condition, the reduction or elimination of symptoms associated with a disease or condition, or the substantial or complete elimination of a disease or condition).

Non-limiting examples of useful therapeutic agents include, but are not limited to, adrenergic agents, adrenocortical steroids, adrenocortical suppressants, alcohol deterrents, aldosterone antagonists, amino acids and proteins, ammonia detoxicants, anabolic agents, analeptic agents, analgesic agents, androgenic agents, anesthetic agents, anorectic compounds, anorexic agents, antagonists, anterior pituitary activators and suppressants, anthelmintic agents, anti-adrenergic agents, anti-allergic agents, antiamoebic agents, anti-androgen agents, anti-anemic agents, anti-anginal agents, anti-anxiety agents, anti-arthritic agents, anti-asthmatic agents, anti-atherosclerotic agents, antibacterial agents, anticholinergic agents, anticholinergic agents, anti-cholinergic agents, anticoagulants, anticoccidial agents, anticonvulsants, antidepressants, antidiabetic agents, antidiuretics, antidotes, antidyskinetics agents, antiemetic agents, antiepileptic agents, anti-estrogen agents, antifibrinolytic agents, antifungal agents, antiglaucoma agents, antihemophilic agents, antihemophilic Factor, antihemorrhagic agents, antihistaminic agents, antihyperlipidemic agents, antihyperlipidemic agents, antihypertensives, antihypertensives, anti-infective agents, anti-inflammatory agents, non-keratinizing agents, antimicrobial agents, antimigraine agents, antimitotic agents, antimycotic agents, antineoplastic agents, anticancer supplementary potentiating agents, antineutropenic agents, antiobsessional agents, antiparasitic agents, antiparkinsonian drugs, antipneumocystic agents, antiproliferative agents, anti-prostatic hypertrophy drugs, antiprotozoal agents, antipruritics, antipsoriatic agents, antipsychotics, antirheumatic agents, antischistosomal agents, antiseborrheic agents, antispasmodic agents, antithrombotic agents, antitussive agents, anti-ulcerative agents, anti-urolithic agents, antiviral agents, benign prostatic hyperplasia therapy agents, blood glucose regulators, bone resorption inhibitors, bronchodilators, carbonic anhydrase inhibitors, cardiac depressants, radioprotectants, cardiotonic agents, cardiovascular agents, choleretic agents, cholinergic agents, cholinergic agonists, cholinesterase deactivators, coccidiostat agents, cognition adjuvants and cognition enhancers, depressants, diagnostic aids, diuretics, dopaminergic agents, ectoparasiticides, emetic agents, enzyme inhibitors, estrogens, fibrinolytic agents, free oxygen radical scavengers, gastrointestinal motility agents, glucocorticoids, gonad-stimulating principles, hemostatic agents, histamine H2 receptor antagonists, hormones, hypocholesterolemic agents, hypoglycemic agents, hypolipidemic agents, hypotensive agents, HMG CoA reductase inhibitors, immunizing agents, immunomodulators, immunoregulators, immunostimulants, immunosuppressants, impotence therapy adjuncts, keratolytic agents, LHRH agonists, luteolysis agents, mucolytics, mucosal protective agents, mydriatic agents, nasal decongestants, neuroleptic agents, neuromuscular blocking agents, neuroprotective agents, NMDA antagonists, non-hormonal sterol derivatives, oxytocic agents, plasminogen activators, platelet activating factor antagonists, platelet aggregation inhibitors, post-stroke and post-head trauma treatments, progestins, prostaglandins, prostate growth inhibitors, prothyrotropin agents, psychotropic agents, radioactive agents, repartitioning agents, scabicides, sclerosing agents, sedatives, sedative-hypnotic agents, selective adenosine A1 antagonists, adenosine A2 receptor antagonists, serotonin antagonists, serotonin inhibitors, serotonin receptor antagonists, steroids, stimulants, thyroid hormones, thyroid inhibitors, thyromimetic agents, tranquilizers, unstable angina agents, uricosuric agents, vasoconstrictors, vasodilators, vulnerary agents, wound healing agents, xanthine oxidase inhibitors, and the like, and combinations thereof.

Useful non-genetic therapeutic agents for use in connection with the present invention include, but are not limited to, (a) anti-thrombotic agents such as heparin, heparin derivatives, urokinase, clopidogrel, and dextro phenylalanine proline arginine chloromethylketone; (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anticoagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promoters; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin; (t) smooth muscle relaxants such as alpha receptor antagonists (e.g., doxazosin, tamsulosin, terazosin, prazosin and alfuzosin), calcium channel blockers (e.g., verapamil, diltiazem, nifedipine, nicardipine, nimodipine and bepridil), beta receptor agonists (e.g., dobutamine and salmeterol), beta receptor antagonists (e.g., atenolol, metoprolol and butoxamine), angiotensin-II receptor antagonists (e.g., losartan, valsartan, irbesartan, candesartan, eprosartan and telmisartan), and antispasmodic/anticholinergic drugs (e.g., oxybutynin chloride, flavoxate, tolterodine, hyoscyamine sulfate, dicyclomine); (u) bARKct inhibitors; (v) phospholamban inhibitors; (w) Serca 2 gene/protein; (x) immune response modifiers including aminoquinolines, for instance, imidazoquinolines such as resiquimod and imiquimod; (y) human apolioproteins (e.g., AI, AII, AIII, AIV, AV, etc.); (z) selective estrogen receptor modulators (SERMs) such as raloxifene, lasofoxifene, arzoxifene, miproxifene, ospemifene, PKS 3741, MF 101 and SR 16234; (aa) PPAR agonists, including PPAR-alpha, gamma and delta agonists, such as rosiglitazone, pioglitazone, neto glitazone, fenofibrate, bexarotene, metaglidasen, troglitazone and tesaglitazar; (bb) prostaglandin E agonists, including PGE2 agonists, such as alprostadil or ONO 8815Ly; (cc) thrombin receptor activating peptide (TRAP); (dd) vaso peptidase inhibitors including benazepril, fosinopril, lisinopril, quinapril, ramipril, imidapril, delapril, moexipril and spirapril; (ee) thymosin beta 4; (ff) phospholipids including phosphorylcholine, phosphatidylinositol and phosphatidylcholine; and (gg) VLA-4 antagonists and VCAM-1 antagonists. The non-genetic therapeutic agents may be used individually or in combination, including in combination with any of the agents described herein.

Further examples of non-genetic therapeutic agents, not necessarily exclusive of those listed above, include taxanes such as paclitaxel (including particulate forms thereof, for instance, protein-bound paclitaxel particles such as albumin-bound paclitaxel nanoparticles, e.g., ABRAXANE), sirolimus, everolimus, tacrolimus, zotarolimus, Epo D, dexamethasone, estradiol, halofuginone, cilostazol, geldanamycin, alagebrium chloride (ALT-711), ABT-578 (Abbott Laboratories), trapidil, liprostin, Actinomycin D, Resten-NG, Ap-17, abciximab, clopidogrel, Ridogrel, beta-blockers, bARKct inhibitors, phospholamban inhibitors, Serca 2 gene/protein, imiquimod, human apolipoprotein, growth factors (e.g., VEGF-2), as well derivatives of the foregoing, among others.

In one or more embodiments, one or more therapeutic agents may be included within or on a polymeric coating, including the micropillars and/or ridges. Plant derivatives such as terpenes, including triterpenes, various acids, boswellic acid, and various phenols and antioxidative plant derivatives may be used.

In one or more embodiments, the base may be formed from the same material as the micropillars and/or the structure of the tissue engagement portion. In one or more embodiments, the micropillars and/or structure may be formed from one material and the base is formed from a different material. In one or more embodiments, the micropillars and/or structure may be formed with layers of material, and these layers may be the same material or may be different materials depending on the characteristics required for the desired frictional engagement of the endoprosthesis with the vessel wall. Differences in surface energy between adjacent hierarchical sites may play a major role in establishing the Wenzel-Cassie interfaces of the present invention, these differences in surface energy may be enhanced by coating some microstructure tips, or domain walls with a thin layer with a desired ionic content.

An endoprosthesis of the present disclosure possesses less abrasive localizing engagement with the lumen wall when inserted into a lumen of the patient, compared to stents relying on frictional engagement. Consequently, removal of the stent may be easier with some traditional removal techniques. In at least one embodiment, the endoprosthesis may be provided with a suture or removal loop on one end of the stent. In at least one embodiment, the removal loop may be provided on a distal end of the stent. It should be noted that references herein to the term "distal" may be to a direction away from an operator of the devices of the present disclosure, while references to the term "proximal" may be to a direction toward the operator of the devices of the present disclosure. While sutures or removal loops are well known in the art for removing endoprosthesis, sutures or removal loops have only been provided on the proximal end of the stent, in other words the closest end to the practitioner. Here, the suture or removal loop may be applied to either end of the endoprosthesis allowing for greater flexibility in using the endoprosthesis as well as greater ease of use. In at least one embodiment, the practitioner may grab the loop from inside the endoprosthesis, and by applying an axial force to the loop, the distal end of the endoprosthesis may be pulled through the lumen of the endoprosthesis itself. This may be known as device inversion. The micropillars may be peeled away from the vessel wall while the stent is flipped inside out to remove the endoprosthesis. This removal technique may be desirable since the surface textures of the present invention have a reduced adhesion when peeled (perpendicular displacement) compared to surface adhesion when undergoing shear (parallel displacement). In other embodiments, the practitioner may grab the loop from outside the endoprosthesis or at an end of the endoprosthesis.

To manufacture the endoprosthesis, several methods can be employed. The polymeric coating may be formed separately from the stent (e.g., as a polymeric film, a hydrogel film, a thin fibrous network, and the like) and then adhered to the stent with an optional adhesive layer disposed between the surface of the stent and the base of the polymeric coating. In one embodiment, the polymeric coating may be formed and adhered to an outer surface of the stent. The optional adhesive layer may be disposed between said outer surface of the stent and a base surface of the coating. In some embodiments, the adhesive layer may be applied to all or at least a portion of one or both of the base surface and the outer surface. The polymeric material may be injected into a mold with the inverse of the micropattern to create the polymeric coating having a micropattern of micro features such as micropillars, textures, and the like. The polymeric material may also be extruded through a mold using a vacuum pump system. In at least one embodiment, the polymeric coating may be created using soft lithography techniques. In one or more embodiments, etching techniques may be used to create the coating, wherein material is taken away from a layer of the coating material to create the micropattern of the polymeric coating. In yet another embodiment, a technique called hot embossing may be used, which involves stamping partially cured polymer into the desired shape of the polymeric coating and then curing it before it is applied to the stent.

Stamping may or may not include the use of a solvent. In one or more embodiments, a stent may be coated by any suitable method (e.g., spraying, dipping, injection molded, and the like), followed by the introduction of textures into the coating after the stent coating. In some embodiments, a fibrous network with micro-scale textures (e.g., voids) may be formed by electrospinning one or more fibers on a pre-coated stent. In one or more embodiments, a laser ablation process may be used to remove material from a coating in order to form one or more micropillars and/or one or more microridges. The laser ablation process may use one or more appropriately sized laser beams which may be selected dependent on the desired pattern to be imparted.

In one embodiment, the implant may be formed by molding the exterior surface modification onto a separate layer of material, such as for example a non-textile material. As used herein, the term "non-textile" and its variants may refer to a material formed by casting, molding, spinning or extruding techniques to the exclusion of typical textile forming techniques, such as braiding, weaving, knitting and the like. Nonlimiting examples of useful polymeric materials for the non-textile polymeric graft portions include polyesters, polypropylenes, polyethylenes, polyurethanes, poly naphthalene, polytetrafluoroethylene, expanded polytetrafluoroethylene, silicone, and combinations and copolymers thereof. In one embodiment, the polymeric material may include polytetrafluoroethylene (PTFE), including expanded polytetrafluoroethylene (ePTFE).

In one embodiment, the stent may comprise an SMP. Examples of SMP's may include but are not limited to polynorbornene and copolymers of polynorbornene, blends of polybornene with KRATON® (thermoplastic elastomer) and polyethylene, styrenic block copolymer elastomers (e.g., styrene-butadiene), polymethylmethacrylate (PMMA), polyethylene, polyurethane, polyisoprene, polycaprolactone and copolymers of polycaprolactone, polylactic acid (PLA) and copolymers of poly lactic acid, polyglycolic acid (PGA) and copolymers of polyglycolic acid, copolymers of PLA and PGA, polyenes, nylons, polycyclooctene (PCO), polyvinyl acetate (PVAc), polyvinylidene fluoride (PVDF), blends of polyvinyl acetate/polyvinylidene fluoride (PVAc/PVDF), blends of polymethylmethacrylate/polyvinyl acetate/polyvinylidene fluoride (PVAc/PVDF/PMMA) and polyvinylchloride (PVC) and blends and/or combinations thereof.

In one or more embodiments, one or more portions of a coating may be deployed into a body lumen separately from a stent. These coatings may be deployed as one or more pads for example. A gluco-adhesive may be applied to an applicable portion of a stent meant to attach to the pre-deployed coating. The radial expansive force of the stent during and after deployment may activate the adhesive and adhere the stent to the coating previously deployed in a body lumen. The gluco-adhesive aspect may comprise be an alginate salt. The alginate salt on a smooth surface may dissolve into the tissue volume and provide temporary adhesive effectiveness. An adhesive disposed on valley sections of a hierarchical texture may serve two purposes: 1) immediate adhesion, and 2) the mucoadhesive serves as a medium that can reinforce domain walls between hydrophilic and hydrophobic regions. Gluco-adhesives may reinforce natural Wenzel-Cassie boundaries, giving a structural aspect to the domain walls rather than simply surfaces of equi-potential. Gluco-adhesives may solidify initially established Wenzel-Cassie domains.

In one or more embodiments, a polymeric coating having negative textures (e.g., microholes) may be formed by using a technique called particulate dissolution wherein a composite material is formed from one or more polymeric materials and one or more particulates followed by dissolving the one or more particulates from the composite material resulting in a composite and/or polymeric material having textures or voids where the one or more particulates were removed. In one embodiment, the particulate dissolution may include salt dissolving wherein the particulates may comprise soluble salts which a dissolved via a solvent. In some embodiments, the salt may be an alginate salt, which may provide capillary effect properties, using ionic concentrations to draw liquids into the voids formed by dissolution.

In one or more embodiments, a polymeric coating having a plurality of textures may be formed by a technique called electrospinning (e.g., using an electrical charge to draw very fine fibers from a liquid), wherein the polymeric coating includes a plurality of fibers arranged at or near the base forming textures between the fibers. The base forming textures may include a network of textures, or a network of voids. A technique called electro writing is a similar concept, except the filament is directed to a target surface in a controlled manner using standard xy-printing technology. When it is desired to produce Wenzel-Cassie structures, a directed electrospinning methodology may lay down individual fibers of different material precisely on top of fibers previously laid down. In at least one embodiment, using this technique allows the stent surface to be comprised of alternating fibers of hydrophilic and hydrophobic materials in alternating arrangement, in stacked fashion, describing a polygonal grid. The polygonal grid for example may include a rectangular grid. These electrospun grid surfaces may provide dual functionality of localizing the stent and promoting a healthy tissue ingrowth, wherein fibrosis may be downregulated, and functional muscle tissue and neovascularization may be upregulated. It is recognized by the applicants that the density of such stacked polygonal mesh may promote a variety of macroscopic tissues, including repair morphologies, kinetic morphologies (e.g., layers of muscle tissue), and pressure walling morphologies. The latter may be important in the repair of lumens that conduct fluids.

In one or more embodiments, the use of salt leaching and/or electrospinning may provide a polymeric coating having one or more textures that form a network of textures. This network of tissues may include a plurality of textures in fluid communication along the base. In some embodiments, cell ingrowth may be enhanced when the polymeric coating includes a network of textures that penetrate the base, or where the base has openings into which tissue is promoted to grow in a sealing aspect. In one or more embodiments, a wide variety of therapeutic agents including, but not limited to growth factors, fibronectin, and others described in other portions of this disclosure herein may be included on, within, and/or in combination with a network of textures to promote tissue ingrowth when the micropatterned polymeric coating contacts tissue.

In at least one embodiment, the coating may be molded as a substantially tubular structure with a lumen defined by the base of the coating. A temporary adhesive layer or alternatively a soft hydrogel layer may be applied to either the stent or to at least a portion of the outer surface of the base of the coating. In at least one embodiment, the adhesive layer may substantially cover the entire outer surface of the base of the coating. The stent may be inserted into the lumen of the coating as a separate element. In at least one embodiment, heat and/or pressure may be applied to ensure proper adhesion of the coating to the stent via an adhesive layer. The adhesive layer may include silicone coatings, other suitable adhesives, or priming solutions that enable the coating to adhere to the metal or polymeric stent (or stent coating thereon).

In one or more embodiments, rather than being molded as a tubular structure, the coating may be molded as a strip attached to the outer surface of the stent. For example, the strip may be disposed in a helical fashion about the stent, or disposed on circumferential rings, or in counter-rotating helical configuration. In some embodiments, the strip may be applied as perimeter strips attached circumferentially about at least a portion of the circumferential perimeter of the stent. In some embodiments, the strip may be a longitudinal strip attached to the stent in a longitudinal direction. In some embodiments, the stent may be helically wrapped about the stent. In some embodiments the coating may be applied as a single strip or as multiple strips. Where the coating is applied as multiple strips, directly adjacent strips may abut one another or may be spaced apart from one another.

In at least one embodiment, the strips may be partial tubular structures that extend along the length of the stent but only cover a portion of the circumference of the stent. In some embodiments, a portion of the stent may be exposed. An adhesive layer may be applied to either the stent or to at least a portion of the base of the coating. In at least one embodiment, heat and/or pressure may be applied to ensure proper adhesion of the coating to the stent via the adhesive layer. In at least one embodiment, discrete micropatterns may be formed on and/or attached directly to either the stent or the polymeric coating.

In one or more embodiments, the polymeric coating may be formed by dip-coating the stent in the coating material without needing an additional adhesive layer to connect the coating to the stent. For example, the stent may be inserted into a mold, which includes a cavity and a tubular member. The cavity may be defined by an inner wall of mold, which is an inverse of the desired micropattern. The stent rests on the tubular member such that the inner surface of the stent is disposed about the tubular member. The mold with the stent may be dipped into the coating material so that the coating material fills the mold and attaches to the stent. In some embodiments, temperature changes and/or pressure changes may be applied to the mold to cure the coating material. Once the coating material cures to form the polymeric coating, the endoprosthesis can be removed from the mold. Alternatively, the polymeric coating may be injection molded onto the stent using a similar mold. The coating material is injected into the mold rather than the mold being dipped into the coating material.

Figure 10:
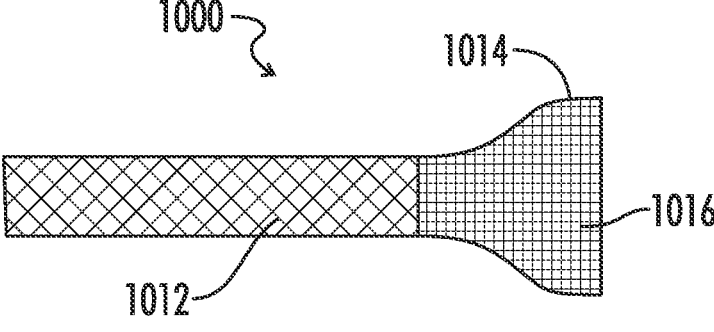
FIG. 10 is a stent that includes at least two electrowritten mesh segments.

Referring now to FIG. 10, an embodiment of a stent 1000 is depicted. The stent 1000 includes at least two electrowritten mesh segments formed in a cylinder. In one embodiment, the segment forms a proximal segment 1012. In one embodiment, the segment forms a distal segment 1014. The two segments 1012 and 1014 may be hollow, generally cylindrical bodies, and formed of mesh filaments 1016. The two segments 1012 and 1014 may be different in structure, manufacture, size, or design. For example, one may be braided by mechanical electro writing means, while another may be crocheted by mechanical electro writing means, or one segment may have layer openings, while the other does not. In addition, the two segments 1012 and 1014 may be made from different materials or they may be made from the same materials. The inner segment 1012 and the outer segment 1014 may be disposed concentrically, with the outer segment 1014 being located on the outside surface of the inner segment 1012. The two segments 1012 and 1014 may be formed from the same continuously interconnected mesh structure formed by the electro writing technique, and may be formed for example by forming a first segment of a stent body and inverting one end of the stent body back upon itself to form a multi-layered, generally cylindrical mesh segment.

In one embodiment, a mesh segment may include two layers. Of course, the two segments 1012 and 1014 may not be made from the same continuously interconnected structure and may be attached by a solvent weld or heat weld, or another non-permanent fixation means. The outer segment 1014 may cover the entire length of the inner segment 1012, or it may cover only a portion of the inner segment 1012. In an alternative embodiment, the outer section 1014 may extend beyond the length of the inner segment 1012. There may be one or more additional layers, such as other stents, coatings or liners, disposed between the inner segment 1012 and the outer segment 1014, or the segments 1012 and 1014 may be disposed directly on each other. Either inner, outer, or both segments may be coated or covered, and may have the same or varying mechanical properties. Use of a double layered stent configuration may provide superior anti-migration abilities. The layers may have additional hierarchical textures disposed on their outer surfaces.

The use of the multiple layer design may aid in anchoring the stent to the implant site, and further aid in the removal of the stent if needed. In addition, the use of the multi-layered design may allow for repositioning of the stent even after it has been implanted. The multiple layer design may also aid in self-sizing of the stent. For example, the stent may include a self-sized area disposed between the inner and outer segments, so that the user may move the layers with respect to each other but not the self-sized area.

A description of some exemplary embodiments of the present disclosure is contained in the following numbered Examples:

Example 1. An endoprosthesis having an expanded state and an unexpanded state, the endoprosthesis comprising: a stent, wherein the stent has an inner surface defining a lumen, an outer surface, a first end, a second end, and a stent thickness defined between the inner surface and the outer surface, wherein the stent defines a plurality of apertures extending through the stent thickness, wherein the apertures are arranged in a macro pattern; and a polymeric coating attached to the outer surface of the stent, the polymeric coating comprising a base comprising a first surface attached to the outer surface of the stent; and a tissue engagement portion comprising a second surface facing outwardly from the stent, the tissue engagement portion comprises a structure that defines a plurality of textures extending inwardly from the second surface toward the base, wherein the textures are arranged in a micropattern, wherein the base and the stent are coterminous, wherein the base covers the apertures of the stent.

Example 2. The endoprosthesis of Example 1, wherein when the endoprosthesis expands in a lumen defined by a vessel wall, the structure defining a plurality of textures arranged in a micropattern applies a force that creates a desired interlock between the vessel wall and the endoprosthesis.

Example 3. The endoprosthesis of Example 1 or Example 2, wherein the shape of the plurality of textures is selected from the group consisting of a cylinder, a rectangular prism, a prism with a polygonal base, a sphere, and an ellipsoid, or any combination thereof.

Example 4. The endoprosthesis of any of Examples 1-3, wherein the plurality of textures of the micropattern are cylindrical microholes or micropillars, each cylindrical texture of the plurality having a diameter and a height.

Example 5. The endoprosthesis of Example 4, wherein the diameter is from about 1 micron to 100 microns.

Example 6. The endoprosthesis of Example 4, wherein the diameter is from about 10 microns to 25 microns.

Example 7. The endoprosthesis of Example 4, wherein the height is from about 1 micron to 100 microns.

Example 8. The endoprosthesis of Example 4, wherein the height is from about 10 microns to 30 microns.

Example 9. The endoprosthesis of Example 4, wherein the diameter of the cylindrical microhole or micropillar is equal to the height of the cylindrical microhole or micropillar.

Example 10. The endoprosthesis of Example 4, wherein each cylindrical microhole or micropillar has a lateral surface, wherein the lateral surface of the cylindrical microhole or micropillar is separated from the lateral surfaces of an adjacent microhole or micropillar by a distance greater than the diameter of the cylindrical microhole or micropillar.

Example 11. The endoprosthesis of Example 1, wherein each texture of the micropattern has a first dimension and a second dimension, wherein the first dimension is from about 1 micron to 100 microns, wherein the second dimension is from about 1 micron to 100 microns, and wherein a ratio between the first dimension and the second dimension is from about 1.1 to 10, and wherein the first micropattern is arranged hierarchically on the second micropattern.

Example 12. The endoprosthesis of any of Examples 1-11, wherein the micropattern is a grid pattern.

Example 13. The endoprosthesis of any of Examples 1-12, wherein the polymeric coating is a polymeric material selected from the group consisting of polyurethanes and silicones, or any combination thereof.

Example 14. The endoprosthesis of any of Examples 1-13, wherein the textures of the micropattern are regularly spaced.

Example 15. The endoprosthesis of any of Examples 1-14, wherein the micropattern includes textures of at least a first configuration and textures of at least a second configuration arranged hierarchically.

Example 16. The endoprosthesis of any of Examples 1-15, wherein the second surface defines a plurality of openings from which the textures extend.

Example 17. The endoprosthesis of Example 16 wherein the plurality of openings comprises a first opening and a second opening and the plurality of textures comprises at least a first texture extending from the first opening and at least a second texture extending from the second opening, wherein the first texture and second texture are in fluid communication via a channel disposed between the first surface and the second surface.

Example 18. The endoprosthesis of any of Examples 1-17, wherein the structure comprises a plurality of intertwining electrowritten fibers.

Example 19. The endoprosthesis of any of Examples 1-18, wherein the structure is adapted to allow controlled cell ingrowth at an implantation site and allow atraumatic endoprosthesis removal from the implantation site after cell ingrowth occurs.

Example 20. The endoprosthesis of any of Examples 1-19, wherein the first surface defines a length and a width of the coating and wherein the second surface of the coating extends around the plurality of textures continuously along at least one of the length and width of the coating.

Example 21. A method of manufacturing an endoprosthesis comprising: forming a polymeric coating, wherein the polymeric coating comprises a base comprising a first surface; and a tissue engagement portion comprising a second surface facing away from the first surface, the tissue engagement portion comprises a structure that defines a plurality of textures extending inwardly from the second surface toward the base, wherein the textures are arranged in a micropattern; and attaching the base of the polymeric coating to an outer surface of a stent, the stent comprising an inner surface defining a lumen.

Example 22. The method of Example 21, wherein the polymeric coating is formed using a mold having an inverse of the micropattern and injecting a polymeric material into the mold.

Example 23. The method of Example 21 or Example 22, wherein attaching the base of the polymeric coating to the outer surface of the stent comprises applying an adhesive layer to at least one of the first surface of the base and the outer surface of the stent.

Example 24. The method of any of Examples 21-23, wherein the polymeric coating is formed in a strip and helically wrapped about the outer surface of the stent.

The above disclosure is intended to be illustrative and not exhaustive. This description will suggest many variations and alternatives to one of ordinary skill in this art. All alternatives and variations are intended to be included within the scope of the claims where the term "comprising" means "including, but not limited to." Those familiar with the art may recognize other equivalents to the specific embodiments described herein which equivalents are also intended to be encompassed by the claims.

Further, the particular features presented in the dependent claims can be combined with each other in other manners within the scope of the present disclosure such that the present disclosure should be recognized as also specifically directed to other embodiments having any other possible combination of the features of the dependent claims.

This completes the description of the preferred and alternate embodiments of the present disclosure. Those skilled in the art may recognize other equivalents to the specific embodiment described herein which equivalents are intended to be encompassed by the claims attached hereto.

Thus, although there have been described particular embodiments of the present invention of a new and useful Biliary Stent it is not intended that such references be construed as limitations upon the scope of this invention except as set forth in the following claims.

What is claimed is:

1. An endoprosthesis for placement in a body lumen comprising:
    a tubular member having a body comprising an interior surface and an exterior surface, at least a portion of the exterior surfacing having disposed thereon a polymer coating, wherein the polymer coating comprises a surface having a first hierarchical microstructure pattern having a first pattern geometry comprising at least a first microtexture and at least a second microtexture;
    the at least first microtexture being hierarchically disposed about the at least second microtexture such that the first hierarchical microstructure pattern is configured to develop a Wenzel interface and a Cassie interface when in contact with a wet surface; and
    the interior surface of the body comprises a second hierarchical microstructure pattern having a second pattern geometry wherein the second pattern geometry is different than the first pattern geometry and does not develop a Wenzel interface and a Cassie interface when in contact with a wet surface.

2. The endoprosthesis of claim 1 wherein the first hierarchical microstructure pattern is capable of adhering to tissue.

3. The endoprosthesis of claim 2 wherein the second hierarchical microstructure pattern is configured to inhibit attachment, or growth, or both, of cellular material to the interior surface.

4. The endoprosthesis of claim 1 wherein the at least first microtexture having a first dimension and a second dimension, each dimension of the first microtexture measuring from 1 micron to 100 microns, and the at least second microtexture having a first dimension and a second dimension wherein the dimension of the second microtexture measuring from 25 microns to 150 microns wherein the first dimension corresponds to a height and the second dimension corresponds to a diameter.

5. The endoprosthesis of claim 1, wherein the body has a constant diameter.

6. The endoprosthesis of claim 2, wherein the polymer coating is disposed about at least 60% of the body.

7. The endoprosthesis of claim 2, wherein the polymer coating is disposed about at least 90% of the body.

8. The endoprosthesis of claim 1, wherein the tubular member comprises a first end and a second end, wherein the first and the second end each respectively include a flared portion.

9. The endoprosthesis of claim 1, wherein the polymer coating is selected from the group consisting of polyester, polylactide, polycarbonate, polyanhydride, and polyimines, or copolymers thereof.

10. The endoprosthesis of claim 1, wherein the polymer coating comprises polymerized hyaluronan.

11. An endoprosthesis for placement in a body lumen, the endoprosthesis comprising:
    a tubular member having a body comprising an inner surface and an outer surface, at least a portion of the outer surface having disposed thereon a polymer coating, wherein the polymer coating is arranged in a concentric pattern around the outer surface, the polymer coating comprising an exterior surface having a first hierarchical microstructure pattern having a first pattern geometry comprising at least a first microtexture and at least a second microtexture, the at least first microtexture being hierarchically disposed about the at least second microtexture such that the first hierarchical microstructure is configured to develop a Wenzel Cassie interface when interacting with a wet surface;
    the inner surface of the body comprises a second hierarchical microstructure pattern having a second pattern geometry wherein the second pattern geometry is different than the first pattern geometry and does not develop a Wenzel interface and a Cassie interface when in contact with a wet surface.

12. The endoprosthesis of claim 11, wherein the body has a constant diameter.

13. The endoprosthesis of claim 12, wherein the polymer coating is disposed about at least 60% of the body.

14. The endoprosthesis of claim 12, wherein the polymer coating is disposed about at least 90% of the body.

15. The endoprosthesis of claim 11, wherein the tubular member comprises a first end and a second end, wherein the first and the second end each respectively include a flared portion.

16. The endoprosthesis of claim 11, wherein the polymer coating is selected from the group consisting of polyester, polylactide, polycarbonate, polyanhydride, and polyimines, or copolymers thereof.

17. The endoprosthesis of claim 11, wherein the polymer coating comprises polymerized hyaluronan.

18. The endoprosthesis of claim 11, wherein the second hierarchical microstructure is anti-fouling.

19. The endoprosthesis of claim 11, wherein the first hierarchical microstructure is tissue adhesive.

20. The endoprosthesis of claim 11, wherein the at least first microtexture has a first dimension and a second dimension from 1 micron to 100 microns, and the at least second microtexture has a first dimension and a second dimension from 25 microns to 150 microns, wherein the first dimension corresponds to a height and the second dimension corresponds to a diameter.

* * * * *